(12) United States Patent
Dellamary et al.

(10) Patent No.: US 8,349,294 B2
(45) Date of Patent: Jan. 8, 2013

(54) STABLE METAL ION-LIPID POWDERED PHARMACEUTICAL COMPOSITIONS FOR DRUG DELIVERY AND METHODS OF USE

(75) Inventors: Luis A Dellamary, San Marcos, CA (US); Jean Riess, Falicon (FR); Ernest G Schutt, San Diego, CA (US); Jeffry G Weers, Belmont, CA (US); Thomas E Tarara, Burlingame, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/967,482

(22) Filed: Dec. 14, 2010

(65) Prior Publication Data

US 2011/0082076 A1 Apr. 7, 2011

Related U.S. Application Data

(63) Continuation of application No. 09/568,818, filed on May 10, 2000, now Pat. No. 7,871,598.

(51) Int. Cl.
*A61K 49/00* (2006.01)
*A61K 9/127* (2006.01)
*A61K 9/14* (2006.01)
*A61K 9/50* (2006.01)
*A61B 5/055* (2006.01)

(52) U.S. Cl. ........ 424/9.32; 424/450; 424/489; 424/502

(58) Field of Classification Search .................. 424/450, 424/502, 489, 9.32, 405
See application file for complete search history.

(56) References Cited

U.S. PATENT DOCUMENTS

| 979,993 | A | 10/1910 | O'Byrne et al. |
| 1,855,591 | A | 4/1932 | Wallerstein |
| 2,457,036 | A | 12/1948 | Epstein |
| 2,797,201 | A | 6/1957 | Veatch et al. |
| 3,014,844 | A | 12/1961 | Thiel et al. |
| 3,362,405 | A | 1/1968 | Hazel |
| 3,555,717 | A | 1/1971 | Chivers |
| 3,619,294 | A | 11/1971 | Black et al. |
| 3,632,357 | A | 1/1972 | Childs |
| 3,655,442 | A | 4/1972 | Schwer et al. |
| 3,745,682 | A | 7/1973 | Wladeisen |
| 3,812,854 | A | 5/1974 | Michaels et al. |

(Continued)

FOREIGN PATENT DOCUMENTS

AU  714998  1/2000

(Continued)

OTHER PUBLICATIONS

Dellamary et al. "Hollow Porous Particles in Metered Dose Inhalers" Pharm Research 17(2): 168-174 (2000).

(Continued)

*Primary Examiner* — San-Ming Hui
(74) *Attorney, Agent, or Firm* — Guy V. Tucker; Janah & Associates, P.C.

(57) ABSTRACT

Microparticle compositions comprising metal ion-lipid complexes for drug delivery are described including methods of making the microparticle compositions and methods of treating certain conditions and disease states by administering the microparticle compositions. The metal ion-lipid complexes can be combined with various drugs or active agents for therapeutic administration. The microparticle compositions of the present invention have superior stability to other microparticle compositions resulting in a microparticle composition with longer shelf life and improved dispersability. The microparticle compositions of the present invention have a transition temperature ($T_g$) of at least 20° C. above the recommended storage temperature (Tst) for drug delivery.

23 Claims, 6 Drawing Sheets

U.S. PATENT DOCUMENTS

Figure 1:
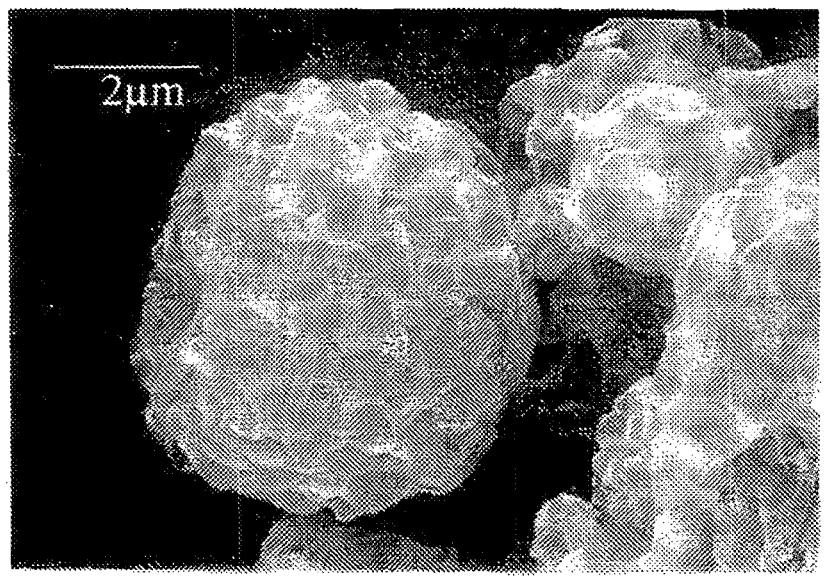

| | | |
|---|---|---|
| 3,948,263 A | 4/1976 | Drake, Jr. et al. |
| 3,957,964 A | 5/1976 | Grimm, III |
| 3,964,483 A | 6/1976 | Mathes |
| 3,975,512 A | 8/1976 | Long, Jr. |
| 4,009,280 A | 2/1977 | Macarthur et al. |
| 4,036,223 A | 7/1977 | Obert |
| 4,089,120 A | 5/1978 | Kozischek |
| 4,098,273 A | 7/1978 | Glenn |
| 4,102,999 A | 7/1978 | Umezawa et al. |
| 4,127,502 A | 11/1978 | Li Mutti et al. |
| 4,127,622 A | 11/1978 | Watanabe et al. |
| 4,158,544 A | 6/1979 | Louderback |
| 4,159,319 A | 6/1979 | Bachmann et al. |
| 4,161,516 A | 7/1979 | Bell |
| 4,180,593 A | 12/1979 | Cohan |
| 4,201,774 A | 5/1980 | Igarashi et al. |
| 4,211,769 A | 7/1980 | Okada et al. |
| 4,244,949 A | 1/1981 | Gupta |
| 4,253,468 A | 3/1981 | Lehmbeck |
| 4,326,524 A | 4/1982 | Drake, Jr. et al. |
| 4,327,076 A | 4/1982 | Puglia et al. |
| 4,327,077 A | 4/1982 | Puglia et al. |
| 4,358,442 A | 11/1982 | Wirtz-Peitz |
| 4,371,557 A | 2/1983 | Oppy et al. |
| 4,397,799 A | 8/1983 | Edgren et al. |
| 4,404,228 A | 9/1983 | Cloosterman |
| 4,407,786 A | 10/1983 | Drake et al. |
| 4,452,239 A | 6/1984 | Malem |
| 4,484,577 A | 11/1984 | Sackner et al. |
| 4,534,343 A | 8/1985 | Nowacki et al. |
| 4,571,334 A | 2/1986 | Yoshida et al. |
| 4,588,744 A | 5/1986 | McHugh |
| 4,590,206 A | 5/1986 | Forrester et al. |
| 4,591,552 A | 5/1986 | Neurath |
| 4,613,500 A | 9/1986 | Suzuki et al. |
| 4,617,272 A | 10/1986 | Kirkwood et al. |
| 4,620,847 A | 11/1986 | Shishov et al. |
| 4,659,696 A | 4/1987 | Hirai et al. |
| 4,680,027 A | 7/1987 | Parsons et al. |
| 4,684,719 A | 8/1987 | Nishikawa et al. |
| 4,701,417 A | 10/1987 | Portenhauser et al. |
| 4,713,249 A | 12/1987 | Schröder |
| 4,721,709 A | 1/1988 | Seth et al. |
| 4,739,754 A | 4/1988 | Shaner |
| 4,758,583 A | 7/1988 | Cerami et al. |
| 4,761,400 A | 8/1988 | Doat et al. |
| 4,762,857 A | 8/1988 | Bollin, Jr. et al. |
| 4,765,987 A | 8/1988 | Bonte et al. |
| 4,790,824 A | 12/1988 | Morrow et al. |
| 4,793,997 A | 12/1988 | Drake et al. |
| 4,812,444 A | 3/1989 | Mitsuhashi et al. |
| 4,814,436 A | 3/1989 | Shibata et al. |
| 4,818,542 A | 4/1989 | DeLuca et al. |
| 4,819,629 A | 4/1989 | Jonson |
| 4,824,938 A | 4/1989 | Koyama et al. |
| 4,830,858 A | 5/1989 | Payne et al. |
| 4,847,079 A | 7/1989 | Kwan |
| 4,855,326 A | 8/1989 | Fuisz |
| 4,861,627 A | 8/1989 | Mathiowitz et al. |
| 4,865,871 A | 9/1989 | Livesey et al. |
| 4,866,051 A | 9/1989 | Hunt |
| 4,883,762 A | 11/1989 | Hoskins |
| 4,891,319 A | 1/1990 | Roser |
| 4,904,479 A | 2/1990 | Illum |
| 4,906,463 A | 3/1990 | Cleary et al. |
| 4,907,583 A | 3/1990 | Wetterlin et al. |
| 4,942,544 A | 7/1990 | McIntosh et al. |
| 4,950,477 A | 8/1990 | Schmitt et al. |
| 4,952,402 A | 8/1990 | Sparks et al. |
| 4,971,787 A | 11/1990 | Cherukuri et al. |
| 4,984,158 A | 1/1991 | Hillsman |
| 4,988,683 A | 1/1991 | Corbiere |
| 4,995,385 A | 2/1991 | Valentini et al. |
| 4,999,384 A | 3/1991 | Roberts et al. |
| 5,006,343 A | 4/1991 | Benson et al. |
| 5,011,678 A | 4/1991 | Wang et al. |
| 5,013,557 A | 5/1991 | Tai |
| 5,017,372 A | 5/1991 | Hastings |
| 5,026,566 A | 6/1991 | Roser |
| 5,026,772 A | 6/1991 | Kobayashi et al. |
| 5,032,585 A | 7/1991 | Lichtenberger |
| 5,033,463 A | 7/1991 | Cocozza |
| 5,043,165 A | 8/1991 | Radhakrishnan |
| 5,049,388 A | 9/1991 | Knight et al. |
| 5,049,389 A | 9/1991 | Radhakrishnan |
| 5,069,936 A | 12/1991 | Yen |
| 5,089,181 A | 2/1992 | Hauser |
| 5,098,893 A | 3/1992 | Franks et al. |
| 5,112,596 A | 5/1992 | Malfroy-Camine |
| 5,112,598 A | 5/1992 | Biesalski |
| 5,118,494 A | 6/1992 | Schultz et al. |
| 5,126,123 A | 6/1992 | Johnson |
| 5,145,684 A | 9/1992 | Liversidge et al. |
| 5,149,543 A | 9/1992 | Cohen et al. |
| 5,149,653 A | 9/1992 | Roser |
| 5,160,745 A | 11/1992 | De Luca et al. |
| 5,173,298 A | 12/1992 | Meadows |
| 5,182,097 A | 1/1993 | Byron et al. |
| 5,190,029 A | 3/1993 | Byron et al. |
| 5,200,399 A | 4/1993 | Wettlaufer et al. |
| 5,202,159 A | 4/1993 | Chen et al. |
| 5,202,333 A | 4/1993 | Berger et al. |
| 5,204,108 A | 4/1993 | Illum |
| 5,208,226 A | 5/1993 | Palmer |
| 5,215,079 A | 6/1993 | Fine et al. |
| 5,225,183 A | 7/1993 | Purewal et al. |
| 5,230,884 A | 7/1993 | Evans et al. |
| 5,239,993 A | 8/1993 | Evans |
| 5,240,712 A | 8/1993 | Smith et al. |
| 5,240,843 A | 8/1993 | Gibson et al. |
| 5,240,846 A | 8/1993 | Collins et al. |
| 5,254,330 A | 10/1993 | Ganderton et al. |
| 5,260,306 A | 11/1993 | Boardman et al. |
| 5,262,405 A | 11/1993 | Girod-Vaquez et al. |
| 5,270,048 A | 12/1993 | Drake |
| 5,284,656 A | 2/1994 | Platz et al. |
| 5,290,765 A | 3/1994 | Wettlaufer et al. |
| 5,299,566 A | 4/1994 | Davis et al. |
| 5,306,483 A | 4/1994 | Mautone |
| 5,306,506 A | 4/1994 | Zema et al. |
| 5,308,620 A | 5/1994 | Yen |
| 5,309,900 A | 5/1994 | Knoch et al. |
| 5,312,335 A | 5/1994 | McKinnon et al. |
| 5,312,909 A | 5/1994 | Driessen et al. |
| 5,342,625 A | 8/1994 | Hauer et al. |
| 5,348,730 A | 9/1994 | Greenleaf et al. |
| 5,348,852 A | 9/1994 | Bonderman |
| 5,354,562 A | 10/1994 | Platz et al. |
| 5,354,934 A | 10/1994 | Pitt et al. |
| 5,366,734 A | 11/1994 | Hutchinson |
| 5,376,359 A | 12/1994 | Johnson |
| 5,380,473 A | 1/1995 | Bogue et al. |
| 5,380,519 A | 1/1995 | Schneider et al. |
| 5,384,345 A | 1/1995 | Naton |
| 5,387,431 A | 2/1995 | Fuisz |
| 5,403,861 A | 4/1995 | Goldwin et al. |
| 5,404,871 A | 4/1995 | Goodman et al. |
| 5,422,360 A | 6/1995 | Miyajima et al. |
| 5,422,384 A | 6/1995 | Samuels et al. |
| 5,425,951 A | 6/1995 | Goodrich, Jr. et al. |
| 5,437,272 A | 8/1995 | Fuhrman |
| 5,451,569 A | 9/1995 | Wong et al. |
| 5,453,514 A | 9/1995 | Niigata et al. |
| 5,458,135 A | 10/1995 | Patton et al. |
| 5,470,885 A | 11/1995 | Fuhrman et al. |
| 5,474,759 A | 12/1995 | Fassberg et al. |
| 5,482,927 A | 1/1996 | Maniar et al. |
| 5,490,498 A | 2/1996 | Faithfull et al. |
| 5,492,688 A | 2/1996 | Byron et al. |
| 5,506,203 A | 4/1996 | Backstrom et al. |
| 5,512,547 A | 4/1996 | Johnson et al. |
| 5,518,709 A | 5/1996 | Sutton et al. |
| 5,518,731 A | 5/1996 | Meadows |
| 5,518,998 A | 5/1996 | Backstrom et al. |
| 5,527,521 A | 6/1996 | Unger |
| 5,540,225 A | 7/1996 | Schutt |
| 5,542,935 A | 8/1996 | Unger et al. |

| | | | | | |
|---|---|---|---|---|---|
| 5,547,656 A | 8/1996 | Unger | 5,780,014 A | 7/1998 | Eljamal et al. |
| 5,547,696 A | 8/1996 | Sorenson | 5,780,295 A | 7/1998 | Livesey et al. |
| 5,552,160 A | 9/1996 | Liversidge et al. | 5,804,212 A | 9/1998 | Illum |
| 5,562,608 A | 10/1996 | Sekins et al. | 5,811,406 A | 9/1998 | Szoka, Jr. et al. |
| 5,567,439 A | 10/1996 | Mters et al. | 5,814,607 A | 9/1998 | Patton |
| 5,569,448 A | 10/1996 | Wong et al. | 5,817,293 A | 10/1998 | Akehurst et al. |
| 5,569,450 A | 10/1996 | Duan et al. | 5,820,883 A | 10/1998 | Tice et al. |
| 5,571,499 A | 11/1996 | Hafler et al. | 5,829,435 A | 11/1998 | Rubsamen et al. |
| 5,580,575 A | 12/1996 | Unger et al. | 5,830,430 A | 11/1998 | Unger et al. |
| 5,580,859 A | 12/1996 | Felgner et al. | 5,830,853 A | 11/1998 | Backstrom et al. |
| 5,589,167 A | 12/1996 | Cleland et al. | 5,849,700 A | 12/1998 | Sorenson et al. |
| 5,591,453 A | 1/1997 | Ducheyne et al. | 5,851,453 A | 12/1998 | Hanna et al. |
| 5,605,673 A | 2/1997 | Schutt et al. | 5,853,698 A | 12/1998 | Straub et al. |
| 5,605,674 A | 2/1997 | Purewal et al. | 5,853,752 A | 12/1998 | Unger et al. |
| 5,607,915 A | 3/1997 | Patton | 5,853,763 A | 12/1998 | Tice et al. |
| 5,611,344 A | 3/1997 | Bernstein et al. | 5,855,913 A | 1/1999 | Hanes et al. .................. 424/489 |
| 5,612,053 A | 3/1997 | Baichwal et al. | 5,856,367 A | 1/1999 | Barrows et al. |
| 5,616,311 A | 4/1997 | Yen | 5,858,784 A | 1/1999 | Debs et al. |
| 5,618,786 A | 4/1997 | Roosdorp et al. | 5,863,554 A | 1/1999 | Illum |
| 5,621,094 A | 4/1997 | Roser et al. | 5,874,063 A | 2/1999 | Briggner et al. |
| 5,631,225 A | 5/1997 | Sorenson | 5,874,064 A | 2/1999 | Edwards et al. |
| 5,635,159 A | 6/1997 | Fu Lu et al. | 5,891,844 A | 4/1999 | Hafner |
| 5,635,161 A | 6/1997 | Adjei et al. | 5,891,873 A | 4/1999 | Colaco et al. |
| 5,642,728 A | 7/1997 | Andersson et al. | 5,898,028 A | 4/1999 | Jensen et al. |
| 5,648,095 A | 7/1997 | Illum et al. | 5,921,447 A | 7/1999 | Barger et al. |
| 5,653,961 A | 8/1997 | McNally et al. | 5,925,334 A | 7/1999 | Rubin et al. |
| 5,653,962 A | 8/1997 | Akehurst et al. | 5,928,469 A | 7/1999 | Franks et al. |
| 5,654,007 A | 8/1997 | Johnson et al. | 5,948,411 A | 9/1999 | Koyama et al. |
| 5,654,278 A | 8/1997 | Sorenson | 5,955,143 A | 9/1999 | Wheatley et al. |
| 5,655,521 A | 8/1997 | Faithful et al. | 5,955,448 A | 9/1999 | Colaco et al. |
| 5,656,297 A | 8/1997 | Bernstein et al. | 5,972,366 A | 10/1999 | Haynes et al. |
| 5,658,549 A | 8/1997 | Akehurst et al. | 5,976,436 A | 11/1999 | Livesley et al. |
| 5,667,808 A | 9/1997 | Johnson et al. | 5,985,309 A | 11/1999 | Edwards et al. |
| 5,667,809 A | 9/1997 | Trevino et al. | 5,993,783 A | 11/1999 | Eljamal et al. |
| 5,673,686 A | 10/1997 | Villax et al. | 5,993,805 A | 11/1999 | Sutton et al. |
| 5,674,471 A | 10/1997 | Akehurst et al. | 5,994,314 A | 11/1999 | Eljamal et al. |
| 5,674,472 A | 10/1997 | Akehurst et al. | 5,994,318 A | 11/1999 | Gould-Fogerite et al. |
| 5,674,473 A | 10/1997 | Purewal et al. | 5,997,848 A | 12/1999 | Patton |
| 5,676,929 A | 10/1997 | Akehurst et al. | 6,013,638 A | 1/2000 | Crystal et al. |
| 5,681,545 A | 10/1997 | Purewal et al. | 6,017,310 A | 1/2000 | Johnson et al. |
| 5,681,746 A | 10/1997 | Bodner et al. | 6,019,968 A | 2/2000 | Platz et al. |
| 5,683,676 A | 11/1997 | Akehurst et al. | 6,034,080 A | 3/2000 | Colaco et al. |
| 5,683,677 A | 11/1997 | Purewal et al. | 6,041,777 A | 3/2000 | Faithful et al. ............ 128/200.24 |
| 5,688,782 A | 11/1997 | Neale et al. | 6,048,546 A | 4/2000 | Sasaki et al. |
| 5,690,954 A | 11/1997 | Illum | 6,051,256 A | 4/2000 | Platz et al. |
| 5,695,743 A | 12/1997 | Purewal et al. | 6,051,259 A | 4/2000 | Johnson et al. |
| 5,695,744 A | 12/1997 | Neale et al. | 6,060,069 A | 5/2000 | Hill et al. |
| 5,698,537 A | 12/1997 | Pruss | 6,068,600 A | 5/2000 | Johnson et al. |
| 5,705,482 A | 1/1998 | Christensen et al. | 6,071,428 A | 6/2000 | Franks et al. |
| 5,707,352 A | 1/1998 | Sekins et al. | 6,077,543 A | 6/2000 | Gordon et al. |
| 5,707,644 A | 1/1998 | Illum | 6,086,376 A | 7/2000 | Moussa |
| 5,718,222 A | 2/1998 | Lloyd et al. | 6,113,948 A | 9/2000 | Heath et al. |
| 5,718,921 A | 2/1998 | Mathiowitz et al. | 6,116,237 A | 9/2000 | Schultz et al. |
| 5,720,940 A | 2/1998 | Purewal et al. | 6,120,751 A | 9/2000 | Unger |
| 5,724,957 A | 3/1998 | Rubsamen et al. | 6,123,924 A | 9/2000 | Mistry et al. |
| 5,725,841 A | 3/1998 | Duan et al. | 6,123,936 A | 9/2000 | Platz et al. |
| 5,725,871 A | 3/1998 | Illum | 6,129,934 A | 10/2000 | Egan et al. |
| 5,728,574 A | 3/1998 | Legg | 6,136,295 A | 10/2000 | Edwards et al. |
| 5,733,555 A | 3/1998 | Chu | 6,136,346 A | 10/2000 | Eljamal et al. |
| 5,735,263 A | 4/1998 | Rubsamen et al. | 6,138,668 A | 10/2000 | Patton et al. |
| 5,736,124 A | 4/1998 | Akehurst et al. | 6,139,819 A | 10/2000 | Unger et al. |
| 5,741,478 A | 4/1998 | Osborne et al. | 6,142,216 A | 11/2000 | Lannes |
| 5,741,522 A | 4/1998 | Violante et al. | 6,150,062 A | 11/2000 | Sugizaki |
| 5,743,250 A | 4/1998 | Gonda et al. | 6,165,463 A | 12/2000 | Platz et al. |
| 5,743,252 A | 4/1998 | Rubsamen et al. | 6,165,508 A | 12/2000 | Tracy et al. |
| 5,744,123 A | 4/1998 | Akehurst et al. | RE37,053 E | 2/2001 | Hanes et al. |
| 5,744,166 A | 4/1998 | Illum | 6,187,344 B1 | 2/2001 | Eljamal et al. |
| 5,747,001 A | 5/1998 | Wiedmann et al. | 6,190,859 B1 | 2/2001 | Putnak et al. |
| 5,747,445 A | 5/1998 | Backstrom et al. | 6,207,135 B1 | 3/2001 | Rossling et al. |
| 5,755,218 A | 5/1998 | Johansson et al. | 6,231,851 B1 | 5/2001 | Platz et al. |
| 5,756,104 A | 5/1998 | de Haan et al. | 6,248,720 B1 | 6/2001 | Mathiowitz et al. |
| 5,766,520 A | 6/1998 | Bronshtein | 6,254,854 B1 | 7/2001 | Edwards et al. |
| 5,766,573 A | 6/1998 | Purewal et al. | 6,258,341 B1 | 7/2001 | Foster et al. |
| 5,770,187 A | 6/1998 | Hasebe et al. | 6,284,282 B1 | 9/2001 | Maa et al. |
| 5,770,222 A | 6/1998 | Unger et al. | 6,290,991 B1 | 9/2001 | Roser et al. |
| 5,770,559 A | 6/1998 | Manning et al. | 6,303,581 B2 | 10/2001 | Pearlman |
| 5,770,585 A | 6/1998 | Kaufman et al. | 6,303,582 B1 | 10/2001 | Eljamal et al. |
| 5,775,320 A | 7/1998 | Patton et al. | 6,309,623 B1 | 10/2001 | Weers et al. |
| 5,776,496 A | 7/1998 | Violante et al. | 6,309,671 B1 | 10/2001 | Foster et al. |

| | | | |
|---|---|---|---|
| 6,313,102 B1 | 11/2001 | Colaco et al. |
| 6,331,310 B1 | 12/2001 | Roser et al. |
| 6,334,182 B2 | 12/2001 | Merchant et al. |
| 6,358,530 B1 | 3/2002 | Eljamal et al. |
| 6,365,190 B1 | 4/2002 | Gordon et al. |
| 6,372,258 B1 | 4/2002 | Platz et al. |
| 6,416,739 B1 | 7/2002 | Rogerson et al. |
| 6,423,334 B1 | 7/2002 | Brayden et al. |
| 6,423,344 B1 | 7/2002 | Platz et al. |
| 6,426,210 B1 | 7/2002 | Franks et al. |
| 6,433,040 B1 | 8/2002 | Dellamary et al. |
| 6,468,782 B1 | 10/2002 | Tunnacliffe et al. |
| 6,479,049 B1 | 11/2002 | Platz et al. |
| 6,503,411 B1 | 1/2003 | Franks et al. |
| 6,503,480 B1 | 1/2003 | Edwards et al. |
| 6,509,006 B1 | 1/2003 | Platz et al. |
| 6,514,496 B1 | 2/2003 | Platz et al. |
| 6,518,239 B1 | 2/2003 | Kuo et al. |
| 6,565,871 B2 | 5/2003 | Roser et al. |
| 6,565,885 B1 | 5/2003 | Tarara et al. |
| 6,569,406 B2 | 5/2003 | Stevenson et al. |
| 6,569,458 B1 | 5/2003 | Gombotz et al. |
| 6,572,893 B2 | 6/2003 | Gordon et al. |
| 6,582,728 B1 | 6/2003 | Platz et al. |
| 6,586,006 B2 | 7/2003 | Roser et al. |
| 6,589,560 B2 | 7/2003 | Foster et al. |
| 6,592,904 B2 | 7/2003 | Platz et al. |
| 6,630,169 B1 | 10/2003 | Bot et al. |
| 6,649,911 B2 | 11/2003 | Kawato |
| 6,652,837 B1 | 11/2003 | Edwards et al. |
| 6,655,379 B2 | 12/2003 | Clark et al. |
| 6,673,335 B1 | 1/2004 | Platz et al. |
| 6,681,767 B1 | 1/2004 | Patton et al. |
| 6,685,967 B1 | 2/2004 | Patton et al. |
| 6,737,045 B2 | 5/2004 | Patton et al. |
| 6,737,066 B1 | 5/2004 | Moss |
| 6,749,866 B2 | 6/2004 | Bernstein |
| 6,752,893 B2 | 6/2004 | Frieder et al. |
| 6,797,258 B2 | 9/2004 | Platz et al. |
| 6,811,792 B2 | 11/2004 | Roser et al. |
| 6,825,031 B2 | 11/2004 | Franks et al. |
| 6,893,657 B2 | 5/2005 | Roser et al. |
| 6,921,527 B2 | 7/2005 | Platz et al. |

FOREIGN PATENT DOCUMENTS

| | | |
|---|---|---|
| EP | 0274431 A2 | 7/1988 |
| EP | 0372777 A2 | 6/1990 |
| EP | 0611567 A1 | 8/1994 |
| FR | 2667072 | 3/1992 |
| WO | WO 9116444 | 10/1991 |
| WO | 9619198 | 6/1996 |
| WO | 9736574 | 10/1997 |
| WO | 9736578 | 10/1997 |
| WO | 9744012 | 11/1997 |
| WO | WO 98/31346 | 7/1998 |
| WO | 9916419 | 4/1999 |
| WO | 9916420 | 4/1999 |
| WO | 9916421 | 4/1999 |
| WO | 9916422 | 4/1999 |
| WO | 0000176 | 1/2000 |
| WO | 0000215 | 6/2000 |
| WO | 0113892 | 3/2001 |

OTHER PUBLICATIONS

Ahlneck et al. "The Molecular Basis of Moisture Effects on the Physical and Chemical Stability of Drugs in the Solid State" Int. J. of Pharmaceutics 62: 87-95 (1990).

Altenbach et al. "$Ca^{2+}$ Binding to Phosphatidycholine Bilayers as Studied by Deuterium Magnetic Resonance. Evidence for the Formation of a $Ca^{2+}$ Complex with Two Phospholipid Molecules" Biochemistry 23: 3913-3920 (1984).

Babincova et al. "Dextran Enhances Calcium-Induced Aggregation of Phosphatidylserine Liposomes: Possible Implications for Exocytosis" Physiol Res 48(4): 319-321 (1999).

Buckton et al. "The Use of Gravimetric Studies to Assess the Degree of Crystallinity of Predominantly Crystalline Powders" Int. J. of Pharmaceutics 123: 265-271 (1995).

Buldt et al. "Neutron Diffraction Studies on Phosphatidylcholine Model Membranes" J. Mol. Biol. 134: 673-691 (1979).

Cevc, G. "Membrane Electrostatics" Biochim Biophys Acta 1031(3): 311-382 (1990)., in particular pp. 330-338.

Duzgunes et al. "Studies on the Mechanism of Membrane Fusion. Role of Head-Group Composition in Calcium- and Magnesium-Induced Fusion of Mixed Phospholipid Vesicles" Biochim Biophys Acta 642: 182-195 (1981).

Ebara et al. "Interactions of Calcium Ions with Phospholipid Membranes" Langmuir 10: 2267-2271 (Apr. 1994).

Eisenberg et al. "Adsorption of Monovalent Cations to Bilayer Membranes Containing Negative Phospholipids" Biochemistry 18(23): 5213-5223 (1979).

Goldbach et al. "Spray-Drying of Liposomes for a Pulmonary Administration I. Chemical Stability of Phospholipids" Drug Develop Ind Pharm 19(19): 2611-2622 (1993).

Gordon et al. "Ideal Copolymers and the Second-Order Transitions of Synthetic Rubbers. I. Non-Crystalline Copolymers" J. Appl. Chem. 2: 493-500 (Sep. 1952).

Hancock et al. "Characteristics and Significance of the Amorphous State in Pharmaceutical Systems" J. of Pharmaceutical Sciences 86(1): 1-12 (Jan. 1997).

Hancock et al. "The Relationship Between the Glass Transition Temperature and the Water Content of Amorphous Pharmaceutical Solids" Pharm Research 11(4): 471-477 (1994).

Hauser et al. "Comparative Structural Aspects of Cation Binding to Phosphatidylserine Bilayers" Biochim Biophys Acts 813: 343-346 (1985).

Hauser et al. "Interactions of Divalent Cations with Phosphatidylserine Bilayer Membranes" Biochemistry 23: 34-41 (1984).

Huster et al. "Investigation of Phospholipid Area Compression Induced by Calcium-Mediated Dextran Sulfate Interaction" Biophys J. 77(2): 879-887 (Aug. 1999).

Huster et al. "Strength of Ca(2+) Binding to Retinal Lipid Membranes: Consequences for Lipid Organization" Biophys J. 78(6): 3011-3018 (Jun. 2000).

Jacobson et al. "Phase Transitions and Phase Separations in Phospholipid Membranes Induced by Changes in Temperature, pH, and Concentration of Bivalent Cations" Biochemistry 14(1): 152-161 (1975).

Kwon et al. "Calcium Ion Adsorption on Phospholipid Bilayers—Theoretical Interpretation" J Jap Oil Chem Soc 43(1): 23-30 (1994).

Lis et al. "Adsorption of Divalent Cations to a Variety of Phosphatidylcholine Bilayers" Biochemistry 20: 1771-1777 (1981).

Lis et al. "Binding of Divalent Cations to Dipalmitoylphosphatidylcholine Bilayers and Its Effect on Bilayer Interaction" Biochemistry 20: 1761-1770 (1981).

Millqvist-Fureby et al. "Surface Characterisation of Freeze-Dried Protein/Carbohydrate Mixtures" Int. J. Pharm. 191: 103-114 (1999).

Millqvist-Fureby et al. "Spray-Drying of Trypsin—Surface Characterisation and Activity Preservation" Int. J. Pharm. 188: 243-253 (1999).

Parasassi et al. "Calcium-Induced Phase Separation in Phospholipid Bilayers. A Fluorescence Anisotrophy" Cellular and Molecul Bio 32(3): 261-266 (1986).

Reboiras, M.D. "Activity Coefficients of $CaCl_2$ and $MgCl_2$ in the Presence of Dipalmitoylphosphatidylcholine-Phosphatidylinositol Vesicles in Aqueous Media" Bioelectrochemistry and Bioenergetics 39: 101-108 (1996).

Royall et al. "Characterisation of Moisture Uptake Effects on the Glass Transitional Behaviour of an Amorphous Drug Using Modulated Temperature DSC" Int. J. Pharm. 192: 39-46 (1999).

Satoh, Koichi. "Determintation of Binding Constants of $Ca^{2+}$, $Na^+$, and $Cl^-$ Ions to Liposomal Membranes of Dipalmitoylphosphatidylcholine at Gel Phase by Particle Electrophoresis" Biochim Biophys Acta 1239: 239-248 (1995).

Seddon, J.M. "Structure of the Inverted Hexagonal ($H_3$) Phase, and Non-Lamellar Phase Transitions of Lipids" Biochim Biophys Acta 1031: 1-69 (1990)., in particular p. 43-44 and 49-50.

I. Joachim Seelig, Handb. Met.-Ligand Interact. Biol. Fluids: Bioinorg. Chem. § Metal Ion Interactions with Lipids: 698-706 (1995).

Shah et al. "The Ionic Structure of Sphingomyelin Monolayers" Biochim Biophys Acts 135: 184-187 (1967).

Shavnin et al. "Cholesterol Affects Divalent Cation-Induced Fusion and Isothermal Phase Transitions of Phospholipid Membranes" Biochim Biophys Acta 946: 405-416 (1988).

Simha et al. "On a General Relation Involving the Glass Temperature and Coefficients of Expansion of Polymers" J. Chem. Physics 37(5): 1003-1007 (Sep. 1962).

Sugisaki et al. "Calorimetric Study of the Glassy State. IV. Heat Capacities of Glassy Water and Cubic Ice" Bulletin of the Chemical Society of Japan 41: 2591-2599 (Nov. 1968).

Tatulian, S.A. "Binding of Alkaline-Earth Metal Cations and Some Anions to Phosphatidyleholine Liposomes" Eur. J. Biochem. 170: 413-420 (1987).

Tatulian, S.A. "Evaluation of Divalent Cation Binding to Phosphatidylserine Membranes by an Analysis of Concentration Dependence of Surface Potential" J. Colloid Interface Science 175: 131-137 (1995).

Verstraeten et al. "Effects of Al(3+) and Related Metals on Membrane Phase State and Hydration: Correlation with Lipid Oxidation" Arch Biochem Biophys 375(2): 340-346 (Mar. 15, 2000).

Whipps et al. "Growth of Calcium Monohydrate at Phospholipid Langmuir Monolayers" J Cryst Growth 192: 243-249 (1998).

Yamaguchi et al. "Adsorption of Divalent Cations onto the Membrane Surface of Lipid Emulsion"0 Colloids and Surfaces B: Biointerfaces 5:49-55 (1995).

Zarif, et al. (1999) Amphotericin B cochleates as a novel oral delivery system for the treatment of fungal infections. Proceedings of the International Symposium on Controlled Release Bioactive Materials. pp. 964-965, XP-002145322.

PCT International Search Report dated Feb. 28, 2002 in 3 pages.

Garrett Reginald H et al "Membrane Phase Transitions" Biochemistry. Saunders College Pub. p. 301-303 (1995).

Kumar Vijay et al "Preparation, characterization, and tabletting properties of a new cellulose-based pharmaceutical aid" Intl J Pharma 235:129-140 (2002).

Ormrod Douglas J et al "Dietary chitosan inhibits hypercholesterolaemia and atherogenesis in the apolipoprotein E-deficient mouse model of atherosclerosis" Atherosclerosis 138:329-334 (1998).

English translation of FR 2667072.

bpm
STABLE METAL ION-LIPID POWDERED PHARMACEUTICAL COMPOSITIONS FOR DRUG DELIVERY AND METHODS OF USE This is a continuation of application Ser. No. 09/568,818 (pending) filed on May 10, 2000, the entire disclosure of which is hereby incorporated by reference.

FIELD OF THE INVENTION

This invention relates to powdered pharmaceutical compositions for drug delivery that exhibit improved stability and dispersability over the shelf life of the composition. More particularly, this invention relates to a highly stable metal ion-lipid microparticle for drug delivery.

BACKGROUND OF THE INVENTION

Powder formulations are the mainstay of drug delivery. Pharmaceutical powders are normally formulated as suspensions, dry powders, tablets, powders for reconstitution and capsules. Pharmaceutical powders are used to facilitate drug delivery because of their ease of use and increase in stability of the active ingredient. However, in the last few years, strict control measures by the FDA and other agencies as to dose uniformity, stability and the prohibition of use of commonly used excipients have threatened certain powder products that are currently on the market. Consequently, this has resulted in greater difficulties in compounding successful powder formulations.

Optimization and control of flow and dispersion characteristics of a powder formulation are of critical importance in the development of powder products and, in particular, powder inhalation products. These characteristics are a function of the principal adhesive forces between particles such as van der waals forces, electrostatic forces and the respective surface tensions of absorbed liquid layers. These forces are influenced by several fundamental physicochemical properties including particle density and size distribution, particle morphology (shape, habit, surface roughness) and surface composition (including absorbed moisture). Interparticle forces that influence flow and dispersion properties are particularly dominant in the micronized or microcrystalline powders that are required for inhalation. Attempts to overcome these forces such as blending a drug with a carrier and adding excipients have been made but have met with limited success. For example, blending a drug with a carrier provides some advantages such as increasing the bulk of the formulation which allows for easier metering of small quantities of potent drugs either at the manufacturing stage or within a delivery device such as a reservoir type device. However, significant disadvantages are evident such as drug/excipient segregation, which severely impacts the dosing and the shelf-life of the composition.

Another approach in drug delivery that has been investigated widely is the incorporation of a drug with excipients by freeze-drying or spray drying. Spray drying is commonly used in the pharmaceutical industry for various substances such as antibiotics, vitamins, vaccines, enzymes, plasma and other excipients as well as for preparation of microcapsules and slow release formulations. Spray drying has gained interest due to the technique's simplicity, low cost, versatility and overall effectiveness. Spray drying is sometimes regarded as a harsh method when compared to freeze-drying due to the high temperature of the drying gas which can be detrimental to sensitive biological materials. However, when considering the spray drying process in greater detail, it is evident that the spray droplets and the dried powder particles maintain a temperature well below the inlet temperature of the drying gas throughout the entire process. As long as water is evaporated from the droplets, a cooling effect is achieved thereby preventing exposure of the product to high temperatures.

Millqvist-Fureby (Int. J. Pharm., 1999, 188, 243-253) has shown the advantages of spray drying trypsin versus freeze-drying where it was demonstrated that the activity loss of trypsin was reduced when it was spray dried instead of freeze-dried. This was explained by the "vitrification" hypothesis which states that it is essential to maintain an excipient in an amorphous or "glassy" state to prevent the protein from changing its shape due to the rigidity of the matrix (Franks, 1991, Biopharma 4, 38-55). These findings, particularly regarding the effect of carbohydrates (most of which tend to crystallize when frozen) and the fact that surface active components experience physical changes in the drying process, which in the case of certain compounds (proteins) are detrimental to functionality of that compound (i.e. activity loss of the protein), show the advantages of spray drying.

Those skilled in the art know that powders have a tendency to be amorphous by nature and that amorphous structures are not stable. Amorphous forms of many drugs and excipients can be produced during processing and revert to the thermodynamically stable crystalline form on storage. The amorphous form will have different physical properties and as such will interact with other phases (i.e. other formulation components, whether these are powders or liquids) in a different manner than that of the crystalline form. An additional complication in systems that contain amorphous material is that the amorphous structure can change under varying conditions and may collapse when exposed to humid air. It has also been known for many years that amorphous materials can collapse when above their glass transition temperature due to the inability of the rubbery material to support its own weight under gravity. For example, lactose is a commonly used excipient which in its amorphous state (micronization, spray drying, freeze-drying, etc.) exhibits varying degrees of structural collapse when held at 50% relative humidity ("RH"). Buckton (1995 Int. J. Pharm. 123, 265-271) noted that water was rapidly absorbed and desorbed by a structure prior to collapse but water sorption to and from the collapsed structure was slow and controlled by diffusion in the solid, rather than just by external relative humidity.

The presence of water in amorphous materials is of importance for two principal reasons. The first reason is called the amplification process (Ahlneck, 1990 Int. J. Pharm., 62, 87-95) which states that a sample containing 0.5% amorphous material and 0.5% associated water will in reality have most of the water absorbed in the amorphous region. If this amorphous excipient material is responsible for maintaining the integrity and the structure of the particle, the physical and chemical stability of the product will be in jeopardy. The second reason water is important is the retention of water in amorphous regions of the sample. Water that is absorbed in a non-collapsed amorphous structure will desorb rapidly and be easily dried; however, if the water is in a collapsed region, this will not hold true and the water will only be able to be removed slowly by diffusion through that region. Once the structure has collapsed, even if the powder is dried, the powder has gone through irreversible transformations that will compromise the integrity of the powder. Thus, water is recognized to be the enemy in the performance and in the physical and chemical stability of most drug formulations including dry powders.

Another important consideration as to the presence of water is the characterization of the effects of sorbed water with glassy drug formulation on the glass transition temperature ("$T_g$"). The relationship between water content and $T_g$ has been explored in a number of publications in the pharmaceutical literature (e.g., Hancock, 1994 Pharm. Res. 11, 471-477). The presence of water is known to lower the $T_g$ of amorphous systems and it has been well established that the presence of water will plasticize the host material leading to a high probability of physical and chemical instability. Andoris (1998 Pharm. Res. 15, 835-842) and Hancock (1997, J Pharm. Sci. 86, 1-12) have addressed the issue of the relationship between storage temperature and the crystallization of amorphous material. These authors have suggested that as long as amorphous materials are stored at approximately 50° C. below their $T_g$, the amorphous materials should be both physically and chemically stable since molecular mobility will be reduced.

The extent of the depression of $T_g$ can be related to the weight fraction of sorbed water. The relationship between moisture uptake and $T_g$ may be described in terms of the Gordon-Taylor relationship (Gordon, 1952, J. Appl. Chem. 2, 493-500). Assuming perfect volume additivity with no specific interaction between the components, the glass transition of the mixture, $T_{g_{mix}}$, is given by the following formula:

$$T_{g_{mix}} = \phi_1 T_{g1} + \phi_2 T_{g2} \quad (1)$$

where $\phi$ is the volume fraction and the subscripts represent the two components. Re-defining the equation in terms of weight fractions, the formula is:

$$T_{g_{mix}} = \frac{(w_1 T_{g1}) + (K w_2 T_{g2})}{w_1 + K w_2} \quad [2]$$

where $w_1$ and $w_2$ are the weight fractions of water and drug respectively and K can be considered to be the ratio of the free volumes of the two components. The $T_g$ of water has been published to be 135° K (Sugisaki 1968, Bull. Chem. Soc. Jpn. 41, 2591-2599) with a K value of 0.198.

Even relatively small amounts of water might be detrimental to the stability of amorphous materials which leads to the question of how much water is necessary to lower the $T_g$ to below the storage temperature, thereby considerably increasing the risk of product failure. The amount of water necessary to lower the $T_g$ to below the storage temperature can be estimated by considering the Simha-Boyer rule:

$$K = \frac{\rho_1 T_{g1}}{\rho_2 T_{g2}} \quad [3]$$

where $\rho_1$ and $\rho_2$ are the densities of materials one and two respectively and $T_{g1}$ and $T_{g2}$ are the glass transition temperatures of materials one and two respectively (Simha, J. Chem. Phys. 1962, 37, 1003-1007).

Royall (Int. J. Pharm. 1999, 192, 39-46) derived an equation that estimates the critical moisture content ($w_c$) which would result in the value of $T_g$ falling to a value 50° K above the storage temperature, thereby providing a much greater margin of safety with regard to the possibility of collapsed structures:

$$w_c = \left[1 + \frac{T_{g2} \rho_2 [T_{ST} - 85]}{135 [T_{g2} - T_{ST} - 50]}\right]^{-1} \quad [4]$$

where $T_{ST}$ is the storage temperature and $T_{g2}$ is the transition temperature of the dry mixture and $\rho_1$ and $\rho_2$ are the densities of materials one and two respectively.

The use of lipids (e.g., free fatty acids and their salts as well as phospholipids) in powder formulations is well accepted in the pharmaceutical industry due to lipids' biotolerability and their physical and chemical characteristics. Polar head groups and surface area of lipids play a functional role at different molecular levels in the context of metal ion-lipid binding. The surface area per lipid molecule together with its electrical charge determines the membrane surface potential $\psi_o$. The electrical charge of the lipid molecule regulates the attraction or repulsion of cations at the lipid-water interface.

The tendency of metal ions to form several coordination bonds with phospholipid head groups can reduce the distance between head groups, thus stretching the hydrocarbon chains into an all-trans conformation. A hydrocarbon chain in the all-trans conformation has a cross-section of approximately 24 Å$^2$, thus yielding a minimum area of about 48 Å$^2$ for a crystalline phospholipid with two hydrocarbon chains. The "crystallization" phenomenon induced by the cation will reduce molecular mobility which is the cause of is instability for certain formulations. In the absence of organization by metal cations, the hydrocarbon chains are disordered, with a direct consequence of lateral expansion of the lipid membrane. In the liquid-crystalline state, the average cross-sectional area for this lipid increases to about 60 Å$^2$ (Büldt, 1979, J. Mol. Biol., 134, 673).

The increase in the chain-melting transition ("crystallization") temperature may exceed 50° C. if the interfacially bound ions have displaced most of the water from the interface. Essentially, anhydrous lipid-ion complexes in excess solution are no exception. One example of this are multivalent metal-ion complexes of diacylphosphatidylserine bilayers (Hauser, 1981, Biochemistry, 23, 34-41). These bilayers form highly ordered, essentially water free bilayers with extremely high transition temperatures in the range between 151-155° C. However, the highest chain-melting phase transition temperatures for diacylphospholipid membranes with monovalent ions or protons bound to the headgroup do not exceed 100° C. due to the lack of strong intermolecular ionic coupling.

Ion-induced phase transition shifts can move in either direction. When a membrane-ion complex binds water more strongly than the membrane surface without bound ions, the ion-induced shift of the bilayer main transition temperature is downwards. This is the case with phosphatidylcholine in the presence of anions or with phosphatidylserine with bound organic counter ions. The chain-melting phase transition temperature for such systems therefore decreases with the increasing bulk electrolyte concentration.

Phospholipid affinity for cations generally follows the sequence:

Lanthanides>transition metals>alkaline earth metals>alkali metals

It is an object of the present invention to provide powdered pharmaceutical compositions for drug delivery that exhibit improved stability and dispersability over the shelf life of the compositions. It is a further object of the invention to avoid the usage of excipients that will reduce the shelf-life of the compositions. It is a further object of the invention to incorporate the drug or active ingredient with the particle avoiding active compound segregation. It is a further object of the invention to provide a novel drug delivery system that is capable of maintaining a high level of dispersability over time.

SUMMARY OF THE INVENTION

The present invention is directed to stable, dry metal ion-lipid microparticle compositions for drug delivery and processes and methods of making the same. The technology is based on the formation of a lipid-metal ion complex matrix that incorporates the drug or active agent to be delivered. The stabilized-particulates or microparticles of the present invention have a lipid concentration of 25-90% w/w, a drug or active agent from 0-80% w/w and a metal concentration from 0-25% w/w. The present invention is also directed to stable powdered metal ion-lipid pharmaceutical compositions wherein the compositions have a $T_g$ of at least 20° C. above the recommended storage temperature ("$T_{ST}$") for drugs and exhibit improved stability and dispersability over the shelf-life of the composition. The present invention is also directed to methods of treating certain diseases or conditions by the therapeutic administration of the microparticle compositions of the present invention.

The present invention is based on the principle that by complexing lipids with metal cations it is possible to substantially change the structure of the lipid by increasing its ordering and by dehydration of the lipid headgroups. This results in a significantly more stable compound which is less susceptible to humidity upon storage than typical spray dried lipid and drug combinations. The physical and chemical stability of the microparticle of the present invention is increased by reducing the disorder in the lipid which consequently reduces the molecular mobility that is the main cause of physical and chemical instability. It is known that amorphous materials (produced by spray drying, micronization, freeze-drying) are unstable and have a tendency to absorb water in order to form much more stable structures (i.e. crystals). Unfortunately, water acts as a plasticizing agent, thereby reducing the glass transition temperature of the powder, increasing the molecular mobility and increasing kinetic processes such as nucleation and crystallization. The resulting low viscosity environments prompt chemical reactions that facilitate chemical degradation.

The increase in stability of the microparticle of the present invention is due to the strong affinity that some metal ions have for lipids. A lipid-metal ion complex will result when the lipids interact with the metal ion. This interaction is known to reduce the distance between the lipid headgroups and, as a consequence, reduce water uptake that is the main cause of dry powder instability. The microparticles of the present invention have shown surprisingly high stability against water sorption when compared to other spray dried formulations.

The process and composition of the present invention involve the formation of an aqueous lipid-cation complex (in the form of a liposome suspension or an emulsion) and a drug or therapeutically or biologically active agent or compound incorporated in the metal ion-lipid complex. By "incorporated", it is intended to mean a combination of the metal ion lipid complex with the drug or active agent to form one unit. The drug or active agent can be engulfed within the metal ion-lipid complex or can predominantly occur on the surface of the composition. Further, incorporation can mean that the drug or active agent can be present as a solution, suspension or solubilized by the lipid. The incorporation process can be achieved by freeze-drying, flash evaporation and most preferably by spray drying. The invention also includes the use of lipids that are generally regarded as safe such as phospholipids and free fatty acid salts. It is also important to understand that the drug or active agent can be a lipid in some instances.

Those skilled in the art will appreciate the increase in stability of the microparticle compositions which is achieved in part by forming the entire particle structure with only one material, which is the lipid-metal ion complex. This material exhibits improved physical and chemical properties in contrast to the commonly used small molecules (e.g. lactose, sucrose, etc.) that when amorphous, are susceptible to moisture and consequently, instability. The microparticles of the present invention have shown surprisingly high dispersion stability in perfluorooctyl bromide (PFOB) and in the non-CFC hydrofluoroalkane propellant HFA 134a that has been approve for medical use. The lyophilic nature (characterized by strong attraction between the colloid medium and the dispersion medium of a colloid system) of the particle components is responsible for the dispersion stability in such non-aqueous media, in addition to the reduced adsorbed water on the particles surface, due in part to the non-hygroscopic nature of the metal ion-lipid complex.

Various metal ions may be used in the metal ion-lipid complex of the present invention such as calcium, magnesium, aluminum, zinc and iron in combination with a salting ion. The metal ion used in the formation of the metal ion-lipid complex includes any metal chosen from lanthanides, transition metals, alkaline earth metals and further including lithium and non-toxic metal ions or any metal ion at non-toxic levels from groups IIa, IIIb and mixtures thereof and all metals from atomic numbers 21-30; 39-48, 57-80 and 89-106. It is also within the scope of the present invention to use a metal containing ion such as $VO^{+2}$. It is also possible to use an organic cation that form dehydrating complexes with phospholipids.

Also included within the scope of the invention are the use of radioisotopes in combination with salting ions such as chloride, nitrates and others. The condition is that the metal ion salt must be able to dissolve in water, which depends on the salt.

The metal ion-lipid combination of the present invention may be comprised of a single lipid or can be mixed with other surfactants to obtain the desired characteristics. Some of the surfactants that can be used are ethoxylated sorbitan esters, sorbitan esters, fatty acid salts, sugar esters, phospholipids, pluronics, tetronics, ethylene oxides, butylene oxides, propylene oxides, cationic surfactants, polyoxyalkylene block copolymers of the to formula $Y[(A)_n\text{–}E\text{–}H]_x$ where A is a polyoxyalkylene moiety, x is at least 2 and Y is derived from water or an organic compound containing x reactive hydrogen atoms, E is a polyoxyethylene moiety, and n can be from 5 to 500. Other classes of surfactants which may be used with the present invention include phosphatidylcholines, egg phosphatides, soy phosphatides, phosphatidylethanolamines, phosphatidylserines, phosphatidylinositols cardiolipin, polymerixable phospholipids, lyso-phosphatidylcholines, lysophosphatides, D-erythro-sphingosines, sphingomyelins, ceramides, cerebrosides, platelet-activation factor (PAF) [Ether ester analogs of phosphatidylcholines], acyl PAF analogs, hydrogenated phospholipids, krill phosphatides, phosphatidic acids, phosphatidylglycerols, phospholipids with multifarious head groups (phosphatidyl methanol, phosphatidylethanol, phosphatidylpropanol, phosphatidylbutanol, etc.), dibromo phosphatidylcholines, mono and diphytanoyl phosphatides, mono and diacetylenic phosphatides, PEG phosphatides, amphipathic antigens phosphatides, mono and diacyl glycerols, mono and diacyl ethylene glycols, mono and diacyl sorbitols, mono and diacyl glycerol succinates, alkyl acyl phosphatides, free fatty acids and salts, fatty alcohols, fatty amines and their salts, fatty ethers, fatty esters, fatty amides, fatty carbonates, cholesterol, cholesterol esters, cholesterol amides and cholesterol ethers.

Other surfactants which may be used are shown in the tables below:

Anionic or Cationic Surfactants Listed in Different Pharmacopoeia or Extra Pharmacopoeia

| Surfactants | Class | Pharmacopoeia/extra pharmacopoeia | | | |
|---|---|---|---|---|---|
| Aluminium monostearate | Anionic | USP/NF | | | Martindale |
| Ammonium lauryl sulfate | Anionic | | | | Martindale |
| Calcium stearate | Anionic | USP/NF | Eur. Ph. | BP | Martindale |
| Dioctyl calcium sulfosuccinate | Anionic | | | | Martindale |
| Dioctyl potassium sulfosuccinate | Anionic | | | | Martindale |
| Dioctyl sodium sulfosuccinate | Anionic | USP/NF | | BP | Martindale |
| Emulsifying wax | Anionic | | Eur. Ph. | BP | Martindale |
| Magnesium lauryl sulfate | Anionic | | | | Martindale |
| Magnesium stearate | Anionic | USP/NF | Eur. Ph. | BP | Martindale |
| Mono-, di-, triethanol-amine lauryl sulfate | Anionic | | | | Martindale |
| Potassium oleate | Anionic | | | | Martindale |
| Sodium castor oil | Anionic | | | | Martindale |
| Sodium cetostearyl sulfate | Anionic | | Eur. Ph. | BP | Martindale |
| Sodium lauryl ether sulfate | Anionic | | | | Martindale |
| Sodium lauryl sulfate | Anionic | USP/NF | Eur. Ph. | | Martindale |
| Sodium lauryl sulfoacetate | Anionic | | | | Martindale |
| Sodium oleate | Anionic | | | | Martindale |
| Sodium stearate | Anionic | USP/NF | | | Martindale |
| Sodium stearyl fumarate | Anionic | USP/NF | | | Martindale |
| Sodium tetradecyl sulfate | Anionic | | | BP | Martindale |
| Zinc oleate | Anionic | | | | Martindale |
| Zinc stearate | Anionic | USP/NF | Eur. Ph. | | Martindale |
| Benzalconium chloride | Cationic | USP/NF | Eur. Ph. | | Martindale |
| Cetrimide | Cationic | | Eur. Ph. | BP | Martindale |
| Cetrimonium bromide | Cationic | | | BP | Martindale |
| Cetylpyridinium chloride | Cationic | USP/NF | Eur. Ph. | BP | Martindale |

Nonionic Surfactants Listed in Different Pharmacopoeia or Extra Pharmacopoeia

| Surfactants | Pharmacopoeia/extra pharmacopoeia | | | |
|---|---|---|---|---|
| Polyols esters | | | | |
| Glyceryl monostearate | USP/NF | Eur. Ph. | BP | Martindale |
| Monodiglyceride | USP/NF | Eur. Ph. | | Martindale |
| Glyceryl monooleate | | | | Martindale |
| Glyceryl behenate | USP/NF | | | Martindale |
| Sorbitan monolaurate | USP/NF | Eur. Ph. | BP | Martindale |
| Sorbitan monopalmitate | USP/NF | Eur. Ph. | | Martindale |
| Sorbitan monooleate | USP/NF | Eur. Ph. | BP | Martindale |
| Sorbitan monostearate | USP/NF | Eur. Ph. | BP | Martindale |
| Sorbitan sesquioleate | USP/NF | | | Martindale |
| Sorbitan trioleate | USP/NF | Eur. Ph. | | Martindale |
| Sorbitan tristearate | | | | Martindale |
| Polysorbate-20 | USP/NF | Eur. Ph. | BP | Martindale |
| Polysorbate-40 | USP/NF | | | Martindale |
| Polysorbate-60 | USP/NF | Eur. Ph. | BP | Martindale |
| Polysorbate-65 | | | | Martindale |
| Polysorbate-80 | USP/NF | Eur. Ph. | BP | Martindale |
| Polysorbate-85 | | | | Martindale |
| Diethylene glycol monostearate | | | | Martindale |
| Ethylene glycol monostearate | | Eur. Ph. | | Martindale |

-continued

Nonionic Surfactants Listed in Different Pharmacopoeia or Extra Pharmacopoeia

| Surfactants | Pharmacopoeia/extra pharmacopoeia | | | |
|---|---|---|---|---|
| Propylene glycol monostearate | USP/NF | Eur. Ph. | | Martindale |
| Self-emulsifying glyceryl stearate | | | BP | |
| Emulsifying wax NF | USP/NF | | | |
| Polyoxyethylene esters and ethers | | | | |
| PEG-40 stearate | USP/NF* | Eur. Ph. | | Martindale |
| PEG-50 stearate | USP/NF* | Eur. Ph. | | Martindale |
| PEG-8 stearate | USP/NF* | Eur. Ph. | | Martindale |
| Polyoxyl-35 castor oil | USP/NF* | Eur. Ph. | | Martindale |
| Polyoxyl-40 hydrogenated castor oil | USP/NF | | | Martindale |
| Laureth-2 | | Eur. Ph. | | Martindale |
| Laureth-4 | | Eur. Ph. | | Martindale |
| Laureth-9 | | Eur. Ph. | | Martindale |
| Ceteareth-20 | | Eur. Ph. | | Martindale |
| Steareth-20 | | Eur. Ph. | | Martindale |
| Oleth-10 | USP/NF* | Eur. Ph. | | Martindale |
| Poloxamers | | | | |
| Poloxamer-188 | USP/NF | | BP | Martindale |
| Poloxamer-407 | USP/NF | | | Martindale |
| Other nonionic surfactants | | | | |
| Nonoxinols-9 | USP/NF | | | Martindale |
| Nonoxinols-10 | USP/NF* | | | Martindale |
| Nonoxinols-11 | | | | Martindale |
| Propylene glycol diacetate | USP/NF* | | | Martindale |
| Polyvinyl alcohol | USP/NF | | | Martindale |

USP/NF* present in USP 23/NF 18 but not in USP 24/NF 19.

The microparticles of the present invention have numerous therapeutic applications in drug delivery. For example, lung surfactant deficient neonates are also known to be calcium deficient and calcium is required for the formation of the "myelin" structures that are required for normal breathing. The administration of a specific metal ion-lipid combination such as Ca-dipalmitoyl phosphatidylcholine ("DPPC") to a neonate using any of the available techniques (nebulization, insufflation, dry powder inhalation, instillation, etc.) will deliver the lipid in the "right" structure and at the same time function as a supply of calcium. Other therapeutic uses for the metal ion-lipid microparticle of the present invention would include use with tobramycin for treating pneumonia, use with ethambutol as a tuberculostatic agent, use in combination with compounds from the sulfonamide family for inhibiting cell metabolism, use for delivery of therapeutic gases, use in combination with antibiotics from the penicillin and cephalosporin family for inhibition of bacterial cell wall synthesis, use in combination with antibiotics of the polymixin and tyrothricin family for interacting with plasma membranes, use with rifamycins, aminoglycosides, tetracyclines and chlorapenicols for disruption of protein synthesis and use in combination with the nalidixic and proflavine antibiotic families for inhibition of nucleic acid transcription and replication. The metal ion-lipid combination of the present invention can also be used in combination with drugs acting on DNA such as actinomycin D, chloroquine and quinine for intercalating cytostatic agents, used in combination with drugs from the mustard family and cis-platin and used in combination with bleomycin for use as a DNA chain cutter.

Other drug or active agents that may be used with the present invention are shown in the table below:

Some Typical Applications of Pharmaceutical Suspensions

| Therapeutic effect | Active compound | Typical concentration (mg/mL) |
|---|---|---|
| Antifungal | Ketoconazole | 20 |
| Antihelminthic | Pirantel pamoate | 50 |
|  | Tiabenzole | 60 |
| Anxiolytic | Diazepam | 0.5 |
| Calcium antagonist | Nicardipine | 20 |
| Antacid | Almagate | 130 |
|  | Aluminum hydroxide | 70 |
|  | Magnesium hydroxide | 200 |
| Antianemic | Folic acid | 10 |
|  | Ferrous gluceptate | 30 |
| Antibacterial | Nalidixic acid | 125 |
|  | Amoxicillin | 50 |
|  | Ampicillin | 50 |
|  | Cefalexin | 50 |
|  | Cefradoxyl | 50 |
|  | Chloramphenicol palmitate | 25 |
|  | Nitrofurantoin | 10 |
| Antiepileptic | Diphenylhydantoin | 25 |
| Cough relief | Codeine | 6 |
|  | Dextromethorfane | 0.5 |
| Anti-inflammatory | Ibuprofen | 20 |
| Antiviral | Acyclovir | 80 |
| Nasal congestion relief | Phenylpropanolamine | 3 |
| Immunological estimulation | Palmidrole | 100 |
| Intestine motility estimulation | Cinitapride | 1 |
| Intestine motility inhibition | Albumin tannate | 50 |

Delivery within the body of certain non-radioactive metals with therapeutic value, such as iron, copper, lithium and certain oligoelements may be accomplished by use of the microparticles of the present invention. The following radioisotopes may also be used in conjunction with the lipid or the lipid-metal ion complex for the medical purposes indicated below:

| Radio-isotope | Symbol | Half-life | Use |
|---|---|---|---|
| Thallium-201 | Tl-201 | 3 days | Diagnostics |
| Gallium-67 | Ga-67 | 3.26 days | Diagnostics |
| Indium-111 | In-111 | 2.8 days | Diagnostics |
| Iodine-123 | I-123 | 13 hours | Diagnostics |
| Palladium-103 | Pd-103 | 17 days | Diagnostics & Therapeutics |
| Molybdenum-99 | Mo-99 | 2.7 days | Diagnostics |
| Xenon-133 | Xe-133 | 5.3 hours | Diagnostics & Therapeutics |
| Iodine-131 | I-131 | 8 days | Diagnostics & Therapeutics |
| Iodine-125 | I-125 | 59.4 days | Therapeutics |
| Fluorine-18 | F-18 | 110 Minutes | Diagnostics |

| Radioisotope | Symbol | Use |
|---|---|---|
| Germanium-68 | Ge-68 | Antibody labeling |
| Cobalt-57 | Co-57 | Instrument calibration |
| Zinc-65 | Zn-65 | Biochemistry |
| Strontium-85 | Sr-85 | Bone tracer |
| Phosphorus-32 | P-32 | Bone cancer therapy |
| Sulfur-35 | S-35 | DNA labeling |
| Yttrium-90 | Y-90 | Radioimmunotherapy |
| Samarium-153 | Sm-153 | Bone cancer therapy |
| Gadolinium-153 | Gd-153 | Osteoporosis/Diagnostic Radiography |
| Ytterbium-169 | Yb-169 | Radiography |
| Chromium-51 | Cr-51 | Blood volume |
| Maganese-54 | Mn-54 | Liver diagnostics |
| Selenium-75 | Se-75 | Biochemistry |
| Tin-113 | Sn-113 | Colon cancer therapy |

The powdered formulations described in the present invention can be applied to inhalation therapies, powders for reconstitution, dry powders and suspensions due to their unique powder stability. By inhalation therapies, we include but are not limited to techniques such as nebulization, insufflation, dry powder inhalation and aerosol inhalation including metered dose inhalers. Administration can include but is not limited to respiratory, pulmonary, otic, anal, optic, vaginal, intramuscular, intravenous, intratracheal, intracuticular, intraperitoneal, nasal, pharyngeal, sinal, subcutaneous, extradural, intracisternal, intrapleural and intrathecal delivery.

The characteristics of the present invention can be modified by using well known compounds described in the literature to modify release kinetics, act as stabilizers or to provide certain surface properties that may be required for specific applications. Examples of such compounds include: polysaccharides; polyvinylpyrrolidone; polyvinyl alcohol; polyethylene glycol; poloxamer block polymers; poloxamines; tetronics; cellulose esters; cellulose ethers; carboxymethylcellulose; hydroxymethylcellulose; carbopol; polyacrylic acids (and salts); crosslinked polyacrylic acids; polylactides; polyglycolides; starches; methylated starches; ethylated starches; crosslinked starches; inulin; dextrins; dextrans; dextran sulfates; cyclodextrins; peptides; polylysine; polyarginine; polyalaninine; polyglycine; and proteins e.g., albumins (bovine, milk, human, egg). Particle morphology can also be manipulated by spray drying conditions, as well as by the ingredients used in the manufacturing of these powdered formulations.

It is well known that in order for a powdered formulation to exhibit good suspension characteristics in a hydrophobic medium (e.g., air, CFC, HFC, PFC), the powder's surface has to be lyophilic (which means that the surface of the particle is able to interact with the suspension media). The stability results from the fact that the lyophilic surface interacts with the suspension media and is thermodynamically stable. Surfactants are known to interact with chlorofluorocarbons, hydrochlorofluorocarbons, hydrofluoroalkanes and to a lesser degree with perfluorocarbons. This interaction is somewhat dictated by the polarizability differences of the suspension media and the components on the surface of the particle. Since surface active compounds tend to reside on the surface of the particles (some drugs or actives also display surface activity that could destabilize the suspension by making the surface lyophobic), the stability of the suspension will be governed by the components on the surface. The use of surfactants in the form of the metal ion-lipid complex as the main building block (in contrast to small molecules that are lyophobic, like lactose) improves the suspension quality of the composition and decreases the susceptibility of the compositions to "melt" when exposed to relatively high moisture environments.

The other contributing factor that affects suspension stability is described by Stokes Law, an equation relating the terminal settling velocity of a sphere in a viscous fluid of known density and viscosity to the diameter of the sphere when subjected to a known force field:

$$V = 2gr^2 \frac{(d_1 - d_2)}{9\mu} \quad [5]$$

where V=velocity of fall (cm s$^{-1}$), g=acceleration of gravity (cm sec$^{-2}$), r="equivalent" radius of particle (cm), d$_1$=density of particle (g mL$^{-1}$), d$_2$=density of medium (g mL$^{-1}$), and μ=viscosity of medium (g cm$^{-1}$ s$^{-1}$). By using metal ion-lipid complexes with densities (measured by He displacement) ranging from 0.5 to 2.0 g cm$^{-3}$, suspension stabilization by density matching will occur in most of the commonly used non-aqueous suspension media. This reduces the speed of sedimentation or creaming of the suspended powder.

The particle inertia of the powdered compositions described in the present invention is low since the density of the lipids used for the building block of the particle is small in comparison to salts. Low inertia means less force to "move" the particles, which will have an impact on their aerodynamic properties.

These particles have shown little particle-particle interaction (in part attributed to the low tendency of the metal ion-lipid to adsorb water), resulting in greater deaggregation when suspending in air or a meter dose inhaler ("MDI") propellant and improved flowability of the powder during processing and in dosing devices.

Advantages of the metal ion-lipid microparticles of the present invention over other spray dried formulations include:

a) Ease of manufacturing—the microparticles of the present invention are produced by a combination of phospholipid dispersions, metal ion solutions and drug preparation followed by spray drying which is a well established pharmaceutical process which is known for its simplicity and versatility;
b) The microparticles of the present invention are produced without the need of the formation of an emulsion or the use of an oil as a blowing agent. This is a significant improvement as to the cost of the final product. Any residual blowing agent in a microparticle could be a source of problems curtailing the release and approval of the product;
c) The microparticles of the present invention are produced without the need of wall-forming agents in contrast to other types of microparticles. Typical spray dried wall forming agents (e.g., lactose, sucrose, mannitol etc.) are very hygroscopic which promotes physical and chemical changes which can render the product useless;
d) The metal ion-lipid complex in the microparticles of the present invention act as a wall forming agent and are non-hygroscopic, making them ideal for inhalable formulations. Since these complexes act as a wall forming agent and are non-hygroscopic, they protect the product against the adverse effects of water;
e) All preferred materials used in the manufacturing of the microparticles of the present invention are generally regarded as safe (GRAS);
f) Due to the versatility in the process and powder characteristic's, a large number of drugs and other material can be incorporated, including heat sensitive proteins and other agents; and,
g) No heating is required to eliminate residual solvents or blowing agents which is a step required in other spray dried formulations that use blowing agents. Heating the final product can cause irreversible damage to the active ingredients and to the powdered formulation itself.

BRIEF DESCRIPTION OF THE DRAWINGS

FIG. 1 is an electron microscopy image of one of the metal ion-phospholipid microparticles of the present invention;

FIG. 2 shows the relationship between the storage temperature and the water content for a sample having a $T_g$ of 80° C. and a sample having a $T_g$ of 120° C. and shows that a content of 10% water will reduce the $T_g$ from 80 to 20° C. and 120 to 50° C.;

FIG. 3 shows the effects of high stress conditions (40° C./75% RH) on pMDIs where sample 6 has the negative effects of the counter-ions that will compete with the metal-lipid complex;

FIG. 4 shows the theoretical relationship between the critical water content (%) calculated from FIG. 4 at which $T_g$ is lowered to the storage temperature as a function of "dry" $T_g$ at a storage temperature of 40° C. for the two different formulations.

FIGS. 5A-5B illustrate Scanning Electron Microscopy images of Sample 8 discussed in Example 10 and shows the high surface area and the cavities on the particles surface; and, FIGS. 6A-6B illustrate Scanning Electron Microscopy images of Sample 9 discussed in Example 10 which show the differences in surface areas of Samples 8 and 9 and the absence of large cavities in Sample 9.

DETAILED DESCRIPTION OF THE INVENTION

The stable dry pharmaceutical composition of the present invention is preferably a dry powder comprised of microparticles that will exhibit a $T_g$ of at least 20° above the recommended $T_{ST}$. The dry powder could be used for but not limited to the preparation of non-aqueous suspensions, powder for reconstitution, dry powders for inhalation, tableting, capsules, ointments, suppositories, creams, and shampoos.

The stable powdered composition of the present invention is mainly made of a metal ion-lipid complex, where the lipid component could be a single lipid or a mixture of several lipids. The preferred lipids are, but are not limited to, phospholipids. The metal can be substituted with a stable or unstable radioisotope, or the radioisotope added in addition to the metal ion-lipid complex, including such radioisotopes as Tc-93, Tc-94, Tc-95, Thallium-201, Gallium-67, Ga-67, Indium-111, Iodine-123, Palladium-103, Molybdenum-99, Iodine-131, Iodine-125, Fluorine-18, Germanium-68, Cobalt-57, Zinc-65, Strontium-85, Phosphorus-32, Sulfur-35, Yttrium-90, Samarium-153, Gadolinium-153, Ytterbium-169, Chromium-51, Maganese-54, Selenium-75 and Tin-113. The metal ion or radioisotope can be chosen depending upon the application.

The stable dry pharmaceutical composition of the present invention can be manufactured by freeze-drying, flash evaporation, grinding and micronizing and most preferably by spray drying. The process involves the formation of an aqueous lipid-cation complex (in the form of a liposome or an emulsion) and a drug or active compound incorporated with the lipid-cation matrix. The drug or active agent may be chosen from the group comprised of antiallergics, antifungals, bronchodilators, pulmonary lung surfactants, analgesics, antibiotics, leukotriene inhibitors or antagonists, antihistamines, antiinflammatories, antineoplastics, anticholinergics, anesthetics, anti-tuberculars, imaging agents, cardiovascular agents, enzymes, steroids, genetic material, viral vectors, antisense agents, proteins, peptides, insulin, albumin, enzymes, genetic material (e.g., DNA, RNA and fragments thereof) pulmozyme, immunoglobulins and combinations thereof. Some specific drugs or active agents include albuterol, albuterol chloride, budesonide, fluticasone propionate, salmeterol xinafoate, formoterol fumarate, nicotine chloride, nicotine nitrate, triamcinolone acetonide, dexamethasone, beclomethasone dipropionate, gentamicin, gentamicin chloride, gentamicin sulfate, ciprofloxacin hydrochloride, Taxol, amphotericin, amikacin, amikacin chloride, Tobramycin, Tobramycin chloride, Tobramycin nitrate.

Although not required for the production of this invention, the use of conventional additives or other ingredients could improve the properties of the powdered formulation is contemplated. Some of these properties are, but are not limited to:
1) Color, taste and appearance by use of colorants and flavorings;
2) Release kinetic modifiers of the particle by use of disintegrants, poloxamers, polysaccharides, polyvinylpyrrolidone, polyvinyl alcohol, polyethylene glycol, PLURONIC block polymers, poloxamers, poloxamines, tetronics, cellulose esters, cellulose ethers, carboxymethylcellulose, hydroxymethylcellulose, carpools, polyacrylic acids (and salts), crosslinked polyacrylic acids, polylactides, polyglycolides, starches, cyclodextrins, methylated starches, ethylated starches, crosslinked starches, inulin, dextrans, dextran sulfates, polyoxyalkylene block copolymers of the formula $Y[(A)_n-E-H]_x$ where A is a polyoxyalkylene moiety, x is at least 2, Y is derived from water or an organic compound containing x reactive hydrogen atoms, E is a polyoxyethylene moiety and n can be from 5 to 500;
3) Peptides, polylysine, polyarginine, polyalanine, polyglycine and proteins such as albumins (e.g., bovine, milk, human, egg), and fatty acid metal salts;
4) Compounds affecting particle morphology and properties are plasticizers, wetting agents and vitrifiers;
5) Preservatives including antioxidants such as BHT, THT, xantofyls, and tocopherol; and,
6) Surface modifiers such as surfactants, including, but not limited to: polyoxyalkylene block copolymers of the formula $Y[(A)_n-E-H]_x$ where A is a polyoxyalkylene moiety, x is at least 2, Y is derived from water or an organic compound containing x reactive hydrogen atoms; E is a polyoxyethylene moiety, n can be from 5 to 500; poloxamers; poloxamines; tetronics; polyvinylpyrrolidone; polyvinyl alcohol; polyethylene glycol; amino acids and bioactive compounds that will bind with a specific receptor in the body such as immunoglobulins, lectins and ligands.

EXAMPLE 1

Metal Ion-Lipid Microparticle without Drug or Active Agent

This Example comprises a typical metal ion-lipid microparticle that is produced using this technology but the microparticle is without the drug or active agent. The microparticle of this Example is shown in FIG. 1. Since the main component of the particle is the lipid, which tends to be more plastic in physical characteristics than most of the excipients normally used, the surface of the particle tends to be highly irregular.

The metal ion-lipid complex based microparticle composition of Example 1 was manufactured by a spray dry process. An aqueous preparation was prepared by mixing two preparations, A and B, immediately prior to spray drying. Preparation A was comprised of a liposome suspension in which 1.1 g of Lipoid SPC-3 (hydrogenated phosphatidylcholines from soy) was dispersed in 25 g of deionized water ("DI water"). Other organic solvents that can be used are DMSO, DMF, EtOH, MeOH, $Et_2O$ and $Me_2O$. The liposome suspension was prepared by first dispersing the phospholipid in hot DI water with a T-25 Ultraturrax at 9000 rpm for about 5 min. The coarse suspension was homogenized under high pressure (18,000 psi) for 5 discrete passes with an Avestin Emulsiflex C5. It is also possible to utilize non-hydrogenated and partially hydrogenated soy and egg phosphatidylcholine as the lipid in these Examples.

Preparation B contained 0.143 g of $CaCl_2.2H_2O$ and 0.21 g of lactose (the lactose was used to mimic a drug) dissolved in 10 g of hot DI water. The combined feed preparation was spray dried with a standard B-191 Mini spray drier under the following conditions: inlet temperature=85° C., outlet temperature=62° C., aspirator=90%, pump=2.2 mL/min, and nitrogen flow=2400 L/h. In practicing the invention, inlet temperatures can vary within the range of approximately −10 to 200° C. and outlet temperatures can vary within the range of approximately −20 to 150° C.

The mean volume aerodynamic particle size of the dry powder was approximately 2.48 μm, measured using an Amherst Aerosizer (Aerosampler module) by dispersing the resulting dry powder with an active dry powder inhaler. Visualization of particle size and morphology was achieved via electron microscopy. The microparticles were first treated with osmium tetraoxide vapor and then affixed on double sticky graphite tape to an aluminum stub. The sample was sputter-coated with a 250 Å layer of gold/palladium, and imaged on a stereoscan 360 SEM (Cambridge, UK Microscope) operated at an accelerating voltage of 20 keV and a probe current of 250 pA.

An example of the microparticle obtained by the method of Example 1 is shown in FIG. 1. In general, the microparticles of this Example had a weight ratio of Phospholipid ("PL") to lactose to calcium chloride ("$CaCl_2.2H_2O$") of about 75:15:10.

EXAMPLE 2

Metal Ion-Lipid Microparticle without Drug or Active Agent

Example 2 shows that in order to fully stabilize the microparticle of the present invention, all of the phospholipid has to be forming a complex with the metal ion.

The metal ion-lipid complex based microparticle composition of this Example was manufactured by a spray dry process. An aqueous preparation was prepared by mixing two preparations, A and B, immediately prior to spray drying. Preparation A was comprised of a liposome suspension in which 1.07 g of distearoyl phosphatidylcholine ("DSPC") was dispersed in 25 g of DI water. The liposome suspension was prepared by first dispersing the phospholipid in hot DI water with a T-25 Ultraturrax at 9000 rpm for about 5 min and then homogenized as in Example 1.

Preparation B contained 0.143 g of $CaCl_2.2H_2O$ and 0.21 g of lactose (the lactose was used to mimic a drug) dissolved in 10 g of hot DI water. While the preparations containing the lipid and metal are usually prepared separately, it is possible to combine the lipid and metal directly.

The combined feed preparation (preparations A and B) was spray dried with a standard B-191 Mini spray drier under the following conditions: inlet temperature=100° C., outlet temperature=67° C., aspirator=90%, pump=2.2 mL/min, nitrogen flow=2400 L/h. The mean volume aerodynamic particle size of the resulting dry powder was approximately 2.91 μm, this was measured using an Amherst Aerosizer (Aerosampler module) by dispersing the dry powder with an active dry powder inhaler. The mean geometric particle size of the powder as measured by the Sympatec particle size analyzer was approximately 2.76 μm. A MDI suspension was done with the powder (0.55% w/w) in HFA 134a. The suspension had the appearance of loose 3D-flocculated material after standing for more than one minute. The particle size was analyzed using the Aerosampler (Amherst) and the mean volume aerodynamic diameter was approximately 3.48 μm.

In general, the microparticles of this Example had a PL:lactose:$CaCl_2.2H_2O$ weight ratio of about 75:15:10.

EXAMPLE 3

Metal Ion-Lipid Microparticle with a Release Kinetic Modifier

Example 3 shows the microparticle of the present invention in conjunction with the release kinetic modifier, polyvinyl pyrrolidone ("PVP"). The use of release kinetic modifiers such as PVP will slow down the release of incorporated drugs.

The metal ion-lipid complex based microparticle composition of Example 3 was manufactured by a spray dry process. An aqueous preparation was prepared by mixing two preparations, A and B, immediately prior to spray drying. Preparation A was comprised of a liposome suspension in which 0.93 g of DSPC was dispersed in 25 g of DI water. The liposome was prepared by first dispersing the phospholipid in hot DI water with a T-25 Ultraturrax at 9000 rpm for about 5 min and then homogenized as in Example 1.

Preparation B contained 0.214 g of $CaCl_2.2H_2O$ and 0.21 g of lactose (the lactose was used to mimic a drug) and 0.071 g of PVP 30K dissolved in 10 g of hot DI water. The combined feed preparation was spray dried with a standard B-191 Mini spray drier under the following conditions: inlet temperature=100° C., outlet temperature=67° C., aspirator=90%, pump=2.2 mL/min and nitrogen flow=2400 L/h. The mean volume aerodynamic particle size of the dry powder was approximately 3.24 μm which was measured using an Amherst Aerosizer (Aerosampler module) by dispersing the dry powder with an active dry powder inhaler. The mean geometric particle size of the powder as measured by the Sympatec particle size analyzer was approximately 2.63 μm. The microparticle of Example 3 had a PL:lactose:$CaCl_2.2H_2O$: PVP weight ratio of about 65:15:15:5.

EXAMPLE 4

Comparison of Various Formulations of Microparticles

In Example 4, three spray dried powders were formulated to compare the effect of formulation, composition and morphology.

A) Sample 1 (Metal Ion Complex with Blowing Agent)

The metal ion-lipid complex based microparticle of this sample was manufactured by a spray dry process. An aqueous preparation was prepared by mixing two preparations, A and B, immediately prior to spray drying. Preparation A was comprised of a fluorocarbon-in-water emulsion in which 29 g of perfluorooctyl bromide, a blowing agent, was dispersed in 27 g of DI water with the aid of 1.32 g of dimyristoyl phosphatidylcholine ("DMPC") emulsifier. The emulsion was prepared by first dispersing the phospholipid in hot DI water with a T-25 Ultraturrax at 9000 rpm for about 5 min. The fluorocarbon was then added dropwise under mixing. The coarse emulsion was homogenized under high pressure (18,000 psi) for 5 discrete passes with an Avestin Emulsiflex C5.

Preparation B contained 0.164 g of $CaCl_2.2H_2O$ and 0.164 g of lactose dissolved in 10 g of hot DI water. The combined feed preparation was spray dried with a standard B-191 Mini spray drier under the following conditions: inlet temperature=75° C., outlet temperature=55° C., aspirator=90%, pump=2.2 mL/min, nitrogen flow=2500 L/h.

The microparticle of sample 1 had a weight ratio of PL:lactose:$CaCl_2.2H_2O$ of about 80:10:10. The mean volume aerodynamic particle size of the dry powder was approximately 2.3 μm which was measured using an Amherst Aerosizer (Aerosampler module) by dispersing the dry powder with an active dry powder inhaler.

B) Sample 2 (Lipid Microparticle and Blowing Agent without Metal Ion)

The lipid based microparticle composition of this sample was manufactured by a spray dry process. An aqueous preparation was prepared by mixing two preparations, A and B, immediately prior to spray drying. Preparation A was comprised of a fluorocarbon-in-water emulsion in which 29 g of perfluorooctyl bromide was dispersed in 27 g of DI water with the aid of 1.32 g of DMPC emulsifier. The emulsion was prepared by first dispersing the phospholipid in hot DI water with a T-25 Ultraturrax at 9000 rpm for about 5 min. The fluorocarbon was then added dropwise under mixing. The coarse emulsion was homogenized under high pressure (18,000 psi) for 5 discrete passes with an Avestin Emulsiflex C5.

Preparation B contained 0.164 g of lactose dissolved in 10 g of hot DI water. The combined feed preparation was spray dried with a standard B-191 Mini spray drier under the following conditions: inlet temperature=75° C., outlet temperature=55° C., aspirator=90%, pump=2.2 mL/min and nitrogen flow=2500 L/h. The mean volume aerodynamic particle size of the dry powder was approximately 3.0 μm which was measured using an Amherst Aerosizer (Aerosampler module) by dispersing the dry powder with an active dry powder inhaler.

The microparticle of sample 2 had a weight ratio of PL:lactose:$CaCl_2$ of about 90:10:0.

C) Sample 3 (Metal Ion Lipid Microparticles without Blowing Agent)

The metal ion-lipid complex based microparticle composition of this sample was manufactured by a spray dry process. An aqueous preparation was prepared by mixing two preparations, A and B, immediately prior to spray drying.

Preparation A was comprised of a liposome suspension of 1.26 g of DMPC dispersed in 28 g of hot DI water with a T-25 Ultraturrax at 9000 rpm for about 5 min. The coarse liposomes were homogenized under high pressure (18,000 psi) for 5 discrete passes with an Avestin Emulsiflex C5.

Preparation B contained 0.164 g of $CaCl_2.2H_2O$ and 0.164 g of lactose dissolved in 10 g of hot DI water. The combined feed preparation was spray dried with a standard B-191 Mini spray drier under the following conditions: inlet temperature=75° C., outlet temperature=55° C., aspirator=90%, pump=2.2 mL/min and nitrogen flow=2500 L/h.

The microparticles of sample 3 had a weight ratio of PL:lactose:$CaCl_2.2H_2O$ of about 80:10:10. The mean volume aerodynamic particle size of the dry powder was approximately 6.4 μm, which was measured using an Amherst Aerosizer (Aerosampler module) by dispersing the dry powder with an active dry powder inhaler.

Approximately 200 mg of each of the samples were transferred to 10 mL empty vials and were labeled as samples 1, 2 and 3. Sample 1 and sample 2 had similar particle morphology (both have very low particle density due to the use of blowing agents). Sample 2 (no calcium in formulation) did not present the formation of the metal ion-lipid complex. Sample 3 (i.e., metal ion-lipid complex formation) had the same formulation as sample 1 but no blowing agent was used. All vials were introduced into a vacuum oven set at 65° C. and the samples were observed for any physical changes. At about 3 minutes, sample 2 started melting and within a few more minutes the entire sample had melted (fused into lumps). Samples 1 and 3 were heated for a total of 30 minutes and no observable physical changes were observed. Samples 1 and 2 had the same particle morphology but sample 2 did not present the formation of the metal ion-lipid complex. Sample 3 (i.e. metal ion-lipid complex formation) had the same formulation as sample 1, but no blowing agent was used. The three formulations demonstrate that stability is dictated by the formation of the metal ion-lipid complex formation and not by the morphology of the particle. Morphology will only affect the density and the aerodynamic size of the particles. Table I summarizes the effect of morphology and metal ion-lipid complexation, on particle size and stability.

| | Mean Volume Aerodynamic Size (μm) | |
|---|---|---|
| Sample ID | Dry Powder | Heated @ 65° C. for 30 min |
| Sample 1[i,ii] | 2.3 | 2.0 |
| Sample 2[i] | 3.0 | Sample fused >8 μm |
| Sample 3[ii] | 6.4 | 5.9 |

[i]Blowing agent used
[ii]Calcium-phospholipid complex

EXAMPLE 5

Metal Ion-Lipid Formation not Affected by Lipophilic Drug

Example 5 shows how a lipophilic drug can be incorporated with the phospholipid, without affecting the formation of the metal ion-lipid complex. It also shows that in order to fully stabilize the particle, the lipid has to be forming a complex with the metal ion.

An aqueous preparation was prepared by mixing two preparations, A and B, immediately prior to spray-drying. Preparation A was comprised of a liposome preparation in which 0.57 g of Indomethacin (Sigma) was previously incorporated with 2.0 g of SPC-3 emulsifier (Hydrogenated soy phosphatidylcholine) by dissolving the Indomethacin and the SPC-3 in 5 mL of methanol followed by evaporation to dryness. This mixture was dispersed in 57 g of DI water. The liposomes were prepared by first dispersing the phospholipid/drug in hot DI water with a T-25 Ultraturrax at 9000 rpm for about 5 min. The liposomes were further homogenized under high pressure (18,000 psi) for 5 discrete passes with an Avestin Emulsiflex C5. In practicing the present invention, the drug or active agent can also be added to the already formed microparticle by conventional means.

Preparation B was comprised of 0.286 g of $CaCl_2.2H_2O$ in 5 g of hot DI water. Preparation A and Preparation B were combined and the combined feed preparation was spray-dried with a standard B-191 Mini spray-drier under the following conditions: inlet temperature=85° C., outlet temperature=59° C., aspirator=83%, pump=2.2 mL/min, nitrogen flow=2400 L/h. The resulting microparticle had a PL:Indomethacin:$CaCl_2.2H_2O$ weight ratio of 70:20:10. The mean volume aerodynamic particle size of the dry powder was of 2.150 μm. This was measured using an Amherst Aerosizer (Aerosampler module) by dispersing the dry powder with an active dry powder inhaler.

The spray dried powder (50 mg) was then hand filled into aluminum canisters (Presspart Inc.) and dried in a vacuum oven at 40° C. (25 mmHg) for 24 hours. The pMDI valves (DF 30/50 Valois) were crimped-sealed onto the canisters (another set was crimped on glass vials) and the canisters were filled with 10 g of HFA-134a (DuPont) by overpressure through the valve stem. Initial particle size was measured using an eight stage Andersen cascade impactor in conformance to USP protocol by measuring the drug concentration in each of the stages of the Andersen cascade impactor. Particle size analysis of the pMDI was of 3.84 μm with a fine particle fraction of 61%. The fine particle fraction is defined as the percentage of drug which is deposited into respirable regions of the lung (i.e., stage 2 through filter [F]), divided by the total amount of drug leaving the device (i.e., stages-1 thought F). The suspension was very stable even after settling for more than one minute, and resembling the aspect of milk.

One hundred mg of the dry powder was then transferred to a 5 mL glass vial and heated for 30 minutes at a temperature of 90° C. The sample was cooled down and 53 mg of sample transferred into an aluminum canister (Presspart Inc.) and dried in a vacuum oven at 40° C. (25 mmHg) for 24 hr. The pMDI valves (DF 30/50 Valois) were crimped-sealed onto the canisters (another set was crimped on glass vials) and the canisters were filled with 10 g of HFA-134a (DuPont) by overpressure through the valve stem. Particle size analysis of the pMDI was of 4.30 μm with a fine particle fraction of 49%

A similar experiment to the above experiment was performed but the microparticle had a PL:Indomethacin:$CaCl_2.2H_2O$ weight ratio of 76:21:3. The particle size of the pMDI for this formulation was 3.93 μm with a fine particle fraction of 56%. When the sample was heated at 90° C. for 30 minutes the entire sample melted within 3 minutes.

EXAMPLE 6

Magnesium Chloride as the Metal

Example 6 shows that other metal ions can be used to stabilize the powders via the formation of the metal ion-lipid complex.

An aqueous preparation was prepared by mixing two preparations, A and B, immediately prior to spray-drying. Preparation A was comprised of a liposome preparation in which 0.54 g of Indomethacin (Sigma) was previously incorporated with 1.92 g of SPC-3 emulsifier (Hydrogenated soy phosphatidylcholine) by dissolving the Indomethacin and the SPC-3 in 5 mL of methanol followed by evaporation to dryness. This mixture was dispersed in 57 g of DI water. The liposomes were prepared by first dispersing the phospholipid/drug in hot DI water with a T-25 Ultraturrax at 9000 rpm for about 5 min. The liposomes were further homogenized under high pressure (18,000 psi) for 5 discrete passes with an Avestin Emulsiflex C5.

Preparation B was comprised of 0.395 g of $MgCl_2.6H_2O$ in 5 g of hot DI water. The combined feed preparation was spray dried with a standard B-191 Mini spray drier under the following conditions: inlet temperature=85° C., outlet temperature=59° C., aspirator=83%, pump=2.2 mL/min, nitrogen flow=2400 L/h. The resulting microparticle had a PL:Indomethacin:$CaCl_2.2H_2O$ weight ratio of 70:20:10. The mean volume aerodynamic particle size of the dry powder was of 2.390 μm, this was measured using an Amherst Aerosizer (Aerosampler module) by dispersing the dry powder with an active dry powder inhaler.

The spray dried powder (50 mg) was hand filled into aluminum canisters (Presspart Inc.) and dried in a vacuum oven at 40° C. (25 mmHg) for 24 hr. The pMDI valves (DF 30/50 Valois) were crimped-sealed onto the canisters (another set was crimped on glass vials) and the canisters were fill with 10 g of HFA-134a (DuPont) by overpressure through the valve stem. The suspension was very stable even after settling for more than one minute, and resembling the aspect of milk. Initial particle size was measured using an eight stage Andersen cascade impactor, in conformance with USP protocol by measuring the drug concentration in each of the stages of the Andersen cascade impactor. Particle size analysis of the pMDI was of 3.93 μm with a fine particle fraction of 56%. The fine particle fraction is defined as the percentage of drug which is deposited into respirable regions of the lung (i.e., stage 2 through filter [F]), divided by the total amount of drug leaving the device (i.e., stages-1 thought F).

EXAMPLE 7

Effect of the Metal Ion on Stability

Two dry pharmaceutical preparations of metal ion-lipid complex based microparticles were manufactured by a spray dry process in order to illustrate the differences in thermal stability of two compositions, sample 4 and sample 5. Sample 4 did not have the required amount of calcium to form the metal ion-lipid complex while sample 5 was formed of a metal ion-lipid complex.

A) Samples 4 and 5

Both samples 4 and 5 were prepared as follows. An aqueous preparation was prepared by mixing two preparations, A and B, immediately prior to spray drying. Preparation A was comprised of 0.75 g of DSPC emulsifier in 25 g of DI water. The preparation was prepared by first dispersing the phospholipid in hot DI water with a T-25 Ultraturrax at 9000 rpm for about 5 min. The coarse emulsion was homogenized under high pressure (18,000 psi) for 5 discrete passes with an Avestin Emulsiflex C5.

Preparation B contained 0.079 g of $CaCl_2.2H_2O$ for sample #4 and 0.165 g of $CaCl_2.2H_2O$ for sample #5 and 0.74 g of lactose dissolved in 10 g of hot DI water. The combined feed preparation was spray dried with a standard B-191 Mini spray drier under the following conditions: inlet temperature=100° C., outlet temperature=70° C., aspirator=90%, pump=2.2 mL/min, nitrogen flow=2500 L/h. The microparticles of sample 4 had a weight ratio of PL:lactose:$CaCl_2.2H_2O$ of about 48:47:5. The microparticles of sample 5 had a weight ratio of PL:lactose:$CaCl_2.2H_2O$ of about 45:45:10.

Approximately 200 mg of each of the dry powders were transferred to 10 mL empty vials and were labeled as samples 4 and 5. Sample 4 had the lowest amount of calcium chloride while sample 5 had the highest. Both vials were introduced into a vacuum oven that was set at 100° C. and the samples were observed for any physical changes. At about 20 minutes, sample 4 started melting and within a few more minutes the entire sample had melted (fused together into lumps). Sample 5 was heated for a total of 60 minutes and no observable physical change was observed. The mean volume aerodynamic particle size of the dry powder (sample 5) was approximately 2.2 μm before and after heating. This was measured using an Amherst Aerosizer (Aerosampler module) by dispersing the dry powder with an active dry powder inhaler.

This Example shows the importance of fully stabilizing the lipid by the formation of the metal ion-lipid complex. Small amounts of calcium act as desiccants and will not modify the packaging of the phospholipid to reduce the harmful effects of water sorption. The amplification process (Ahlneck 1990, Int. J. Pharm., 62, 87-95) is a second reason to fully stabilize the lipid by the formation of the metal ion-lipid complex.

EXAMPLE 8

Effect of Moisture on Stability of Microparticles

This Example showed that if the samples exemplified in Example 7 are exposed to water and absorb water vapor, the plasticizing effect of water decreases its $T_g$ approximately following the Gordon-Taylor equation:

$$T_{g_{mix}} = \frac{(w_1 T_{g1}) + (K w_2 T_{g2})}{w_1 + K w_2} \qquad [6]$$

Figure 2:
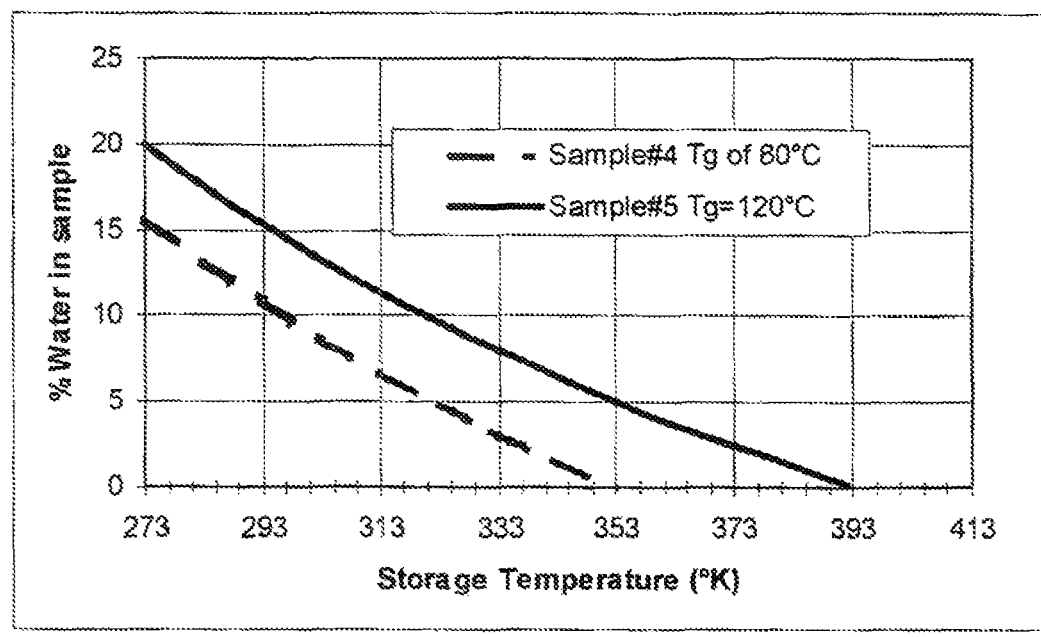

Referring to FIG. 2, the graph demonstrates the relationship between the storage temperature and water content and exemplifies what would be the effect of the decrease in $T_g$ by the amount of water that has been absorbed. If 10% water is absorbed by both powders, sample 4 would decrease its $T_g$ from 80° C. to 20° C. Consequently, the resulting particle would be likely to be very unstable if the powder is stored at 40° C. In contrast, sample 5 would decrease its $T_g$ from 120° C. to about 50° C. and would be much more stable even if stored at 40° C.

EXAMPLE 9

Effect of a Counter Ion on Thermal Stability

In Example 9, two dry pharmaceutical preparations microparticles are manufactured by a spray dry process in order to illustrate the differences in thermal stability of both compositions (one having the negative effect of the counter-ions that will compete with the metal-lipid complex [sample 6], while the other sample [sample 7] does not).

A) Sample 6 (Metal Ion-Lipid Microparticle with Counter Ion that Impedes the Complex Formation)

An aqueous preparation was prepared by mixing three preparations (preparations A, B and C) immediately prior to spray drying. Preparation A was comprised a fluorocarbon-in-water emulsion in which 191 g of perfluorooctyl bromide was dispersed in 198 g of DI water with the aid of 4.75 g of DSPC emulsifier. The emulsion was prepared by first dispersing the phospholipid in hot DI water with a T-25 Ultraturrax at 9000 rpm for about 5 min. The fluorocarbon was then added dropwise under mixing. The coarse emulsion was homogenized under high pressure (18,000 psi) for 5 discrete passes with an Avestin Emulsiflex C5.

Preparation B contained 0.413 g of $CaCl_2.2H_2O$ dissolved in 5 g of DI water. Preparation C contained 5.17 g of albuterol sulfate USP ("Al") (bronchodilator) dissolved in 46 g of hot DI water. The combined feed preparation was spray dried with a standard B-191 Mini spray drier under the following conditions: inlet temperature=85° C., outlet temperature=61° C., aspirator=82%, pump=2.2 mL/min, nitrogen flow=2500 L/h. The resulting microparticle of sample 6 had a PL:Al:$CaCl_2.2H_2O$ weight ratio of about 46:50:4. Sample 6 is the same formulation as described in Dellamary, 2000, 17 Pharm. Res., 2, 168-174.

This sample shows that calcium addition to a formulation will not always result in the formation of a metal ion-lipid complex. If the counter ion competes with the formation of the metal ion-lipid complex, the final product will not show an improvement in the $T_g$ that is responsible for the stability of the powder against the harmful effects of water sorption. Calcium, in the form of calcium sulfate in the sample, is simply acting as a desiccant and does not modify the packaging of the phospholipid to reduce the harmful effects of water sorption.

B) Sample 7 (Metal Ion-Lipid Microparticle without Counter Ion)

An aqueous preparation is prepared by mixing preparations A and B immediately prior to spray drying. Preparation A comprises a liposome suspension in which 5.714 g of distearoylphosphatidylcholine (DSPC) is dispersed in 190 g of DI. The liposome is prepared by first dispersing the phospholipid in hot DI water with a T-25 Ultraturrax at 9000 rpm for about 5 min. The coarse liposome suspension is homogenized under high pressure (18,000 psi) for 5 discrete passes with an Avestin Emulsiflex C5.

Preparation B contains 0.95 g of $CaCl_2.2H_2O$, and 2.86 g of micronized albuterol free base dissolved/suspended in 16 g of hot DI water. The combined feed preparation is spray dried with a standard B-191 Mini spray drier under the following conditions: inlet temperature=85° C., outlet temperature=61° C., aspirator=85%, pump=2.2 mL/min, nitrogen flow=2400 L/h. The resulting microparticle of sample 7 has a PL:Albuterol:$CaCl_2.2H_2O$ weight ratio of about 60:30:10.

Both samples are dried in an oven at 60° C. for one hour prior to any experiment. Approximately 200 mg of each of the dry powders are transferred to 10 mL empty vials and were labeled as samples 6 and 7. Sample 6 had the albuterol sulfate that competes with the effective binding of the calcium to the phospholipid while sample 7 has no compound to compete with the calcium-phospholipid complex. Sample 6 was introduced into a vacuum oven that was set at 100° C. and the sample was observed for any physical changes. At about 25 minutes, sample 6 started melting and within a few more minutes, the entire sample had melted. Sample 7 is expected to have a glass transition temperature above 100° C., since there is not counter ions that will impede the formation of the metal-ion lipid complex. A differential scanning calorimeter assay (Mettler Toledo Star) was performed on samples 6 showing a transition temperature at 58° C. (corresponding to the gel-liquid crystalline transition of DSPC) for sample 6.

The spray dried powder of sample 6 was then hand filled into aluminum canisters (Presspart Inc.) and dried in a vacuum oven at 40° C. (25 mmHg) for 3-4 hr. The pMDI valves (BK RB700 Bespak Inc.) was crimped-sealed onto the canisters and a Pamasol (Pfäffikon) model 2005 was used to fill the canisters with HFA-134a (DuPont) by overpressure through the valve stem. Initial particle size was measured using an eight stage Andersen cascade impactor, in conformance to USP protocol by measuring the drug concentration in each of the stages of the Andersen cascade impactor. The cans were stored in an incubator and held at 40° C. and 75% RH in accordance to the USP for accelerated stability. Samples were taken at time points of 1, 3 and 6 months. Particle size was measured using the Andersen cascade impactor. Mass median aerodynamic diameters (MMAD) and geometric standard deviations (GSD) were evaluated by fitting the experimental cumulative function to a log-normal distribution with two-parameter fitting routine (Scientist, MicroMath):

$$\text{Mass} = \frac{1 + \text{erf}\left(\frac{\ln D_{aer} - \ln MMAD}{\ln GSD}\right)}{2} \quad [7]$$

where the dependent variable is the mass of drug deposited on a given stage and the independent variable, $D_{aer}$, is the aerodynamic diameter value for a given stage according to manufacture.

Figure 3:
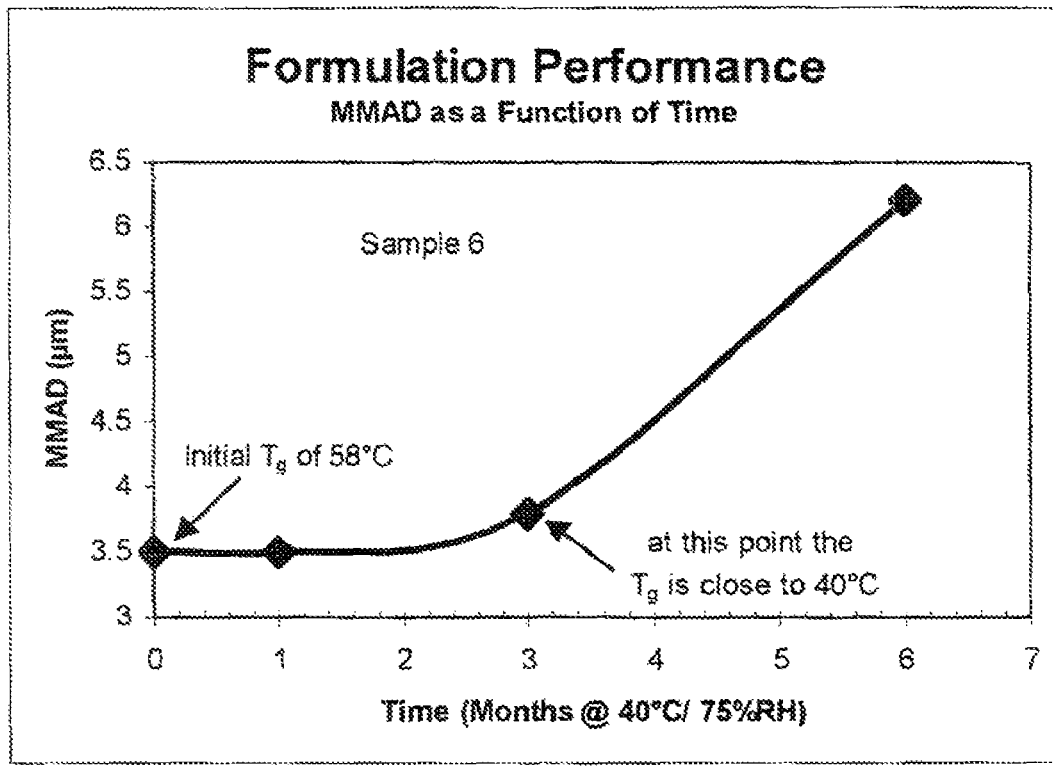
Figure 4:
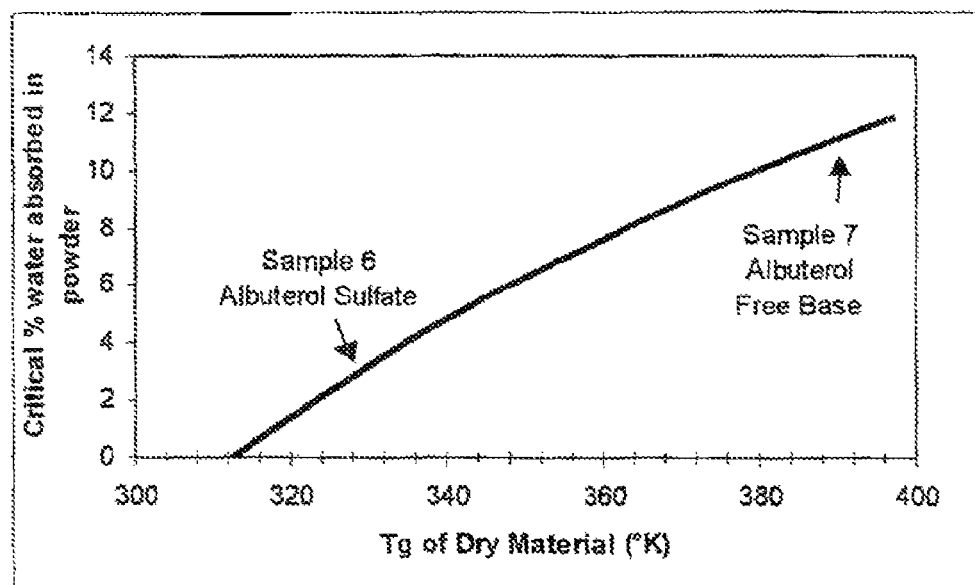

FIG. 3 shows the effects of high stress conditions (40° C./75% RH) on pMDIs where sample 6 has the negative effects of the counter-ions that will compete with the metal-lipid complex. Sample 6 had a $T_g$ of about 58°. Increasing the $T_g$ to about 90° C. or above by the promoting the formation of the metal ion-phospholipid complex, it will be possible to prevent the loss in formulation performance after storage that is seen with formulation 6. FIG. 4 shows the theoretical relationship between the critical water content (%) calculated from FIG. 4 at which $T_g$ is lowered to the storage temperature as a function of "dry" $T_g$ at a storage temperature of 40° C. for the two different formulations. The albuterol sulfate formulation that impedes the formation of the calcium-phospholipid complex can only absorb up to 3% water before the structure collapses at a temperature of 40° C., while the albuterol free base formulation that does not impede the calcium-phospholipid complex can withstand (theoretically based on the Gordon-Taylor equation) up to 11% by weight water at 40° C.

It is contemplated that using larger amounts of highly soluble metal ions will overcome the negative effect of the counter ion. By manufacturing the preparation with albuterol free base (Sample 7) instead of the albuterol sulfate (sample 6), it is expected that the negative action of the sulfate ions on the calcium can be eliminated.

EXAMPLE 10

Metal Ion-Lipid Microparticle with Budesonide with and without Blowing Agent

Example 10 shows the suspension stability and dispersability of budesonide formulated in calcium-phospholipid complex with and without blowing agent.

A) Sample 8 (Metal Ion-Lipid Microparticle with Blowing Agent)

An aqueous preparation was prepared by mixing two preparations, A and B, immediately prior to spray drying. Preparation A was comprised of a fluorocarbon-in-water emulsion in which 26 g of perfluorooctyl bromide was dispersed in 33 g of DI water with the aid of 1.30 g of SPC-3 emulsifier (hydrogenated soy phosphatidylcholine). The emulsion was prepared by first dispersing the phospholipid in hot DI water with a T-25 Ultraturrax at 9000 rpm for about 5 min. The fluorocarbon was then added dropwise under mixing. The coarse emulsion was homogenized under high pressure (18,000 psi) for 5 discrete passes with an Avestin Emulsiflex C5.

Preparation B contained 0.162 g of $CaCl_2.2H_2O$ and 0.162 g of budesonide dissolved/suspended in 4 g of hot DI water. The combined feed preparation was spray dried with a standard B-191 Mini spray drier under the following conditions: inlet temperature=85° C., outlet temperature=62° C., aspirator=100%, pump=2.2 mL/min, nitrogen flow=2400 L/h. The resulting microparticle of sample 8 had a PL:budesonide:CaCl$_2$.2H$_2$O weight ratio of about 80:10:10. The mean volume aerodynamic particle size of the dry powder was approximately 4.1 μm, this was measured using an Amherst Aerosizer (Aerosampler module) by dispersing the dry powder with an active dry powder inhaler.

B) Sample 9 (Metal Ion-Lipid Microparticle without Blowing Agent)

An aqueous preparation was prepared by mixing two preparations, A and B, immediately prior to spray drying. Preparation A was comprised of a liposome suspension in which 1.90 g of SPC-3 emulsifier (hydrogenated soy phosphatidylcholine) was dispersed in 47 g of DI water. The liposomes were prepared by first dispersing the phospholipid in hot DI water with a T-25 Ultraturrax at 9000 rpm for about 5 min. The coarse liposomes were homogenized under high pressure (18,000 psi) for 5 discrete passes with an Avestin Emulsiflex C5.

Preparation B contained 0.238 g of CaCl$_2$.2H$_2$O and 0.238 g of budesonide dissolved/suspended in 4 g of hot DI water. The combined feed preparation was spray dried with a standard B-191 Mini spray drier under the following conditions: inlet temperature=85° C., outlet temperature=62° C., aspirator=100%, pump=2.2 mL/min, nitrogen flow=2400 l/hr. The mean volume aerodynamic particle size of the dry powder was approximately 4.2 μm, this was measured using an Amherst Aerosizer (Aerosampler module) by dispersing the dry powder with an active dry powder inhaler. The resulting microparticle of sample 9 had a PL:budesonide:CaCl$_2$.2H$_2$O weight ratio of about 80:10:10.

The spray dried powders (50 mg) were then hand filled into aluminum canisters (Presspart Inc.) and dried in a vacuum oven at 40° C. (25 mmHg) for 24 hr. The pMDI valves (DF 30/50 Valois) were crimped-sealed onto the canisters (another set was crimped on glass vials) and the canisters were filled with approximately 10 mg of HFA-134a (DuPont) by overpressure through the valve stem. Initial particle size was measured using an eight stage Andersen cascade impactor, in conformance to USP protocol, by measuring the drug concentration in each of the stages of the Andersen cascade impactor.

The fine particle fraction is defined as the percentage of drug which is deposited into respirable regions of the lung (i.e., stage 2 through filter (F)), divided by the total amount $$FPF = \frac{100 \sum_{i=2}^{F} m_i}{\sum_{i=-1}^{F} m_i}$$

of drug leaving the device (i.e., stages-1 through F). Table II summarizes the particle sizing of budesonide formulated in the metal ion-phospholipid complex in pMDIs using HFA 134a.

| | VMAD[1] (μm) | MMAD[2] (μm) | GSD[3] (μm) | FPF[4] (%) |
|---|---|---|---|---|
| Sample 8 | 2.44 | 3.99 | 1.81 | 59 |
| Sample 9 | 3.87 | 4.57 | 1.94 | 48 |

[1]Volume mean aerodynamic diameter (Amherst Aerosizer)
[2]Mean mass aerodynamic diameter (Andersen Cascade)
[3]Geometric standard deviation (Andersen Cascade)
[4]Fine particle fraction (Andersen Cascade)

Figure 5A:
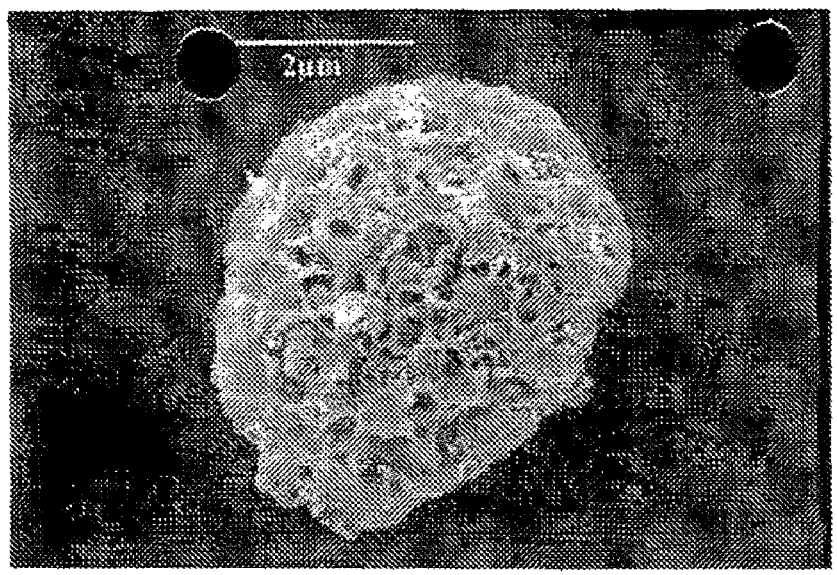
Figure 5B:
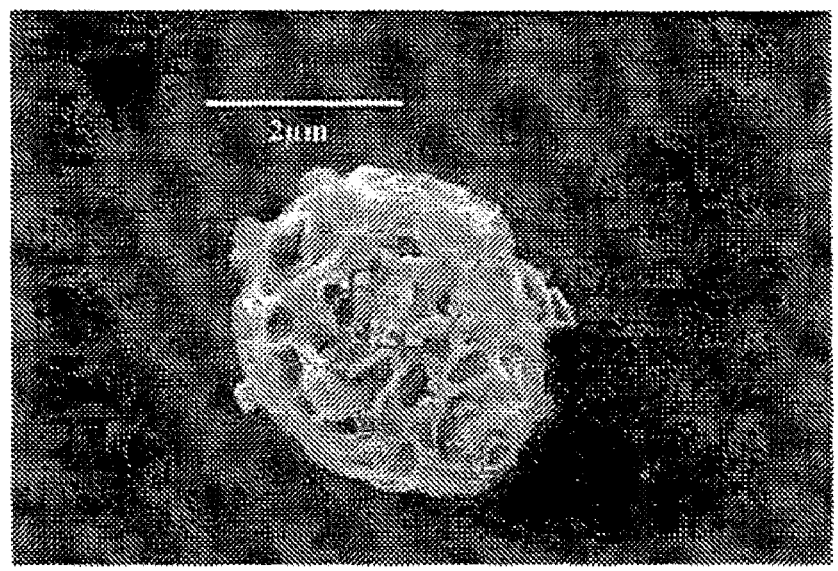

Scanning Electron Microscopy Images of sample 8 (with blowing agent) are shown in FIGS. 5A and 5B. Note the high surface area and the cavities on the particles surface. The cavities are approximately half spheres.

The powders were then tested in a dry powder inhaler (FlowCaps, Hovione Lisbon, Portugal). A modification of the USP protocol was employed to minimize particle bouncing and entrainment. Plates 2 through 7 were inverted, loaded with a Gelman #60010 A/E glass fiber filter and 4 mL DI water was dispensed onto them. The powders were actuated from the Hovione FlowCaps DPI device for 5 seconds into a 28.3 L/min vacuum source. The Andersen impactor was then disassembled and extracted with 100% methanol. The extract was centrifuged at 14,000 rpm for 30 minutes in order to separate any glass fiber that could interfere with the assay. Budesonide quantitation was performed by UV spectrophotometry at a wavelength of 242 nm against a blank. Table II Summarizes the particle sizing of budesonide formulated in the metal ion-phospholipid complex using a passive dry powder inhaler (FlowCaps, Hovione).

| | MMAD[1] (μm) | GSD[2] (μm) | FPF[3] (%) | Emitted Dose % |
|---|---|---|---|---|
| Sample 8 | 4.81 | 2.09 | 57 | 92 |
| Sample 9 | 4.57 | 1.94 | 48 | 88 |

[1]Mean mass aerodynamic diameter (Andersen Cascade)
[2]Geometric standard deviation (Andersen Cascade)
[3]Fine particle fraction (Andersen Cascade)

Figure 6A:
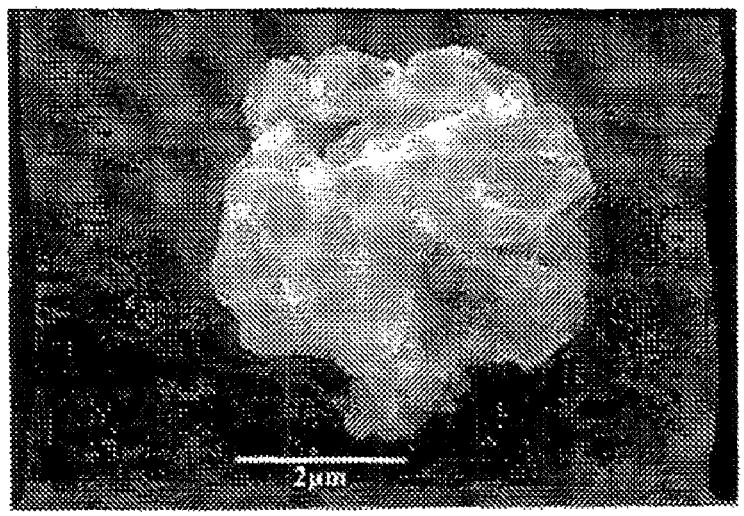
Figure 6B:
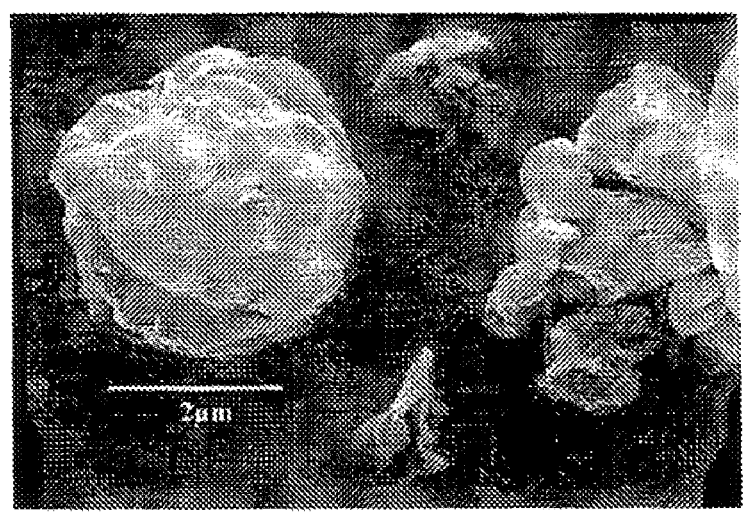

Scanning Electron Microscopy Images of sample 9 (no blowing agent) are shown in FIGS. 6A and 6B. Note the surface area and the absence of large cavities on sample 9 in FIGS. 6A and 6B in comparison to sample 8 which is shown on FIGS. 5A and 5B.

The only difference between samples 8 and 9 is that sample 8 was manufactured with a blowing agent to reduce particle density. Bulk density measurements of sample 8 and sample 9 were 0.03 and 0.1 g/ml, respectively. Both samples 8 and 9 showed good performance when evaluated as pMDIs and dry powder inhalers. The main difference observed between both particles was their bulk density, which can be attributed to the extensive cavitation seen on sample 8 (FIGS. 5A and 5B). The surface of the microparticles in sample 9 as shown in FIGS. 6A and 6B is wrinkled without a large number of open pores due to the plastic nature of the metal ion-lipid complex. Both suspensions in propellant HFA 134a resembled a milky appearance even after the samples were settled for more than one minute.

EXAMPLE 11

Metal Ion-Lipid Microparticle with Hemocyanin

Example 11 shows the feasibility of producing metal ion-lipid complex microparticles containing large proteins, while maintaining the activity of the protein.

The metal ion-lipid complex based microparticle composition of this Example were manufactured by a spray dry process. An aqueous preparation was prepared by mixing three preparations A, B and C immediately prior to spray drying. Preparation A was comprised of 0.75 g of Lipoid EPC3 (hydrogenated egg-phosphatidylcholine) emulsifier in 40 g of DI water. The liposome was prepared by first dispersing the phospholipid in hot DI water with a T-25 Ultraturrax at 9000 rpm for about 5 min. The coarse liposome was homogenized under high pressure (18,000 psi) for 5 discrete passes with an Avestin Emulsiflex C5.

Preparation B contained 0.107 g of $CaCl_2.2H_2O$ and 0.107 g of lactose dissolved in 10 g of hot DI water. Preparation C contained 10 mg of hemocyanin, keyhole limpet from *megathura crenulata* (MW $3\times10^6$–$7.5\times10^6$), that was dissolved in 2 mL of Dulbecco's PBS buffer. Preparations A and B were combined and an aliquot (6.5 g) of this preparation was mixed with the protein preparation C. The combined feed preparation was spray dried with a standard B-191 Mini spray drier under the following conditions: inlet temperature=85° C., outlet temperature=62° C., aspirator=90%, pump=2.2 mL/min, nitrogen flow=2500 L/h. The resulting microparticle had a PL:Hemocyanin:$CaCl_2.2H_2O$ weight ratio of about 80:10:10. Activity of the protein was confirmed by an ELISPOT bioassay technique, where the T cells ability to produce cytokines was measured in the presence and in the absence of microparticles. The results were compared to freshly prepared hemocyanin, the activity of the hemocyanin incorporated in the microparticles was of the same magnitude as the standard hemocyanin preparation.

EXAMPLE 12

Metal Ion-Lipid Microparticle with Insulin

Example 12 shows the incorporation of insulin with the phospholipid-metal ion of the present invention for treatment of diabetes and where the phospholipid-metal ion serves as a penetrater enhancer for the pulmonary delivery of insulin. Since the insulin is already incorporated into a lung surfactant type of media, the insulin absorption into the lung tissue should be enhanced by this situation.

The stable dry pharmaceutical preparation metal ion-lipid based microparticle of this Example was manufactured by a spray dry process. An aqueous preparation was prepared by mixing two preparations, A and B, immediately prior to spray drying. Preparation A was comprised of a liposome dispersion in which 1.71 g of hydrogenated soy phosphatidylcholine was dispersed in 50 g of DI water. The liposome dispersion was prepared by first dispersing the phospholipid in hot DI water with a T-25 Ultraturrax at 9000 rpm for about 5 min. Preparation B contained 0.286 g of $CaCl_2.2H_2O$ and 0.86 g of insulin zinc salt (Sigma) in 10 g of DI water. The insulin zinc salt was dissolved by acidifying with 1 M HCl. The combined feed solution was spray dried with a standard B-191 mini spray drier under the following conditions: inlet temperature=85° C.; outlet temperature=63° C.; aspirator=85%; pump=2.2 ml/min; nitrogen flow=2400 L/hr. The resulting microparticle had a PL:$CaCl_2.2H_2O$: Insulin weight ratio of 60:10:30.

EXAMPLE 13

Single Preparation Feedstock

The particles of Example 10, sample 9 are prepared by dispensing the phospholipid (SPC-3) in a single aqueous preparation containing all of the solutes ($CaCl_2.2H_2O$ and budesonide) in the combined 51 g of hot DI water and homogenizing and spray drying as in Example 10, sample 9. Particles similar to sample 9 of Example 10 were obtained.

EXAMPLE 14

Increased Density and Refractive Index [Polarizability] Particles

The method of Example 10, sample 9 is employed to produce particles with four times higher $CaCl_2.H_2O$ concentration, with a PL:budesonide:$CaCl_2.2H_2O$ weight ratio of about 61:30:9 by substituting 0.952 g of $CaCl_2.H_2O$ for the 0.238 g of budesonide employed in the previous experiment. The excess calcium chloride, in addition to forming metal ion-lipid complexes, increases the density of the final particles to more closely match that of MDI propellants and reduces the creaming rate to yield more accurate dosing. A second effect is to increase the refractive index and therefore the polarizability of the particles to more closely match the polarizability of the MDI propellants and reduce the tendency of the particles toward aggregation. It is expected that a similar effect would be obtained by adding 0.714 g of sodium chloride to the formula of sample 9 in Example 10. These formulas would be most advantageous where consistent MDI dosing is most important.

EXAMPLE 15

Slow Dissolving Particle Employing the Formation of Calcium Carbonate

The particles of Example 11 are prepared as in Example 11 with the exception that four times the $CaCl_2.H_2O$ is employed and thus 0.428 g of $CaCl_2.H_2O$ is substituted for the 0.107 g of $CaCl_2.H_2O$ utilized in Example 11. The particles thus formed are then exposed to carbon dioxide either in the spray dryer gas stream while forming the particles or in a gas/vacuum chamber after the particles are formed. Slowly dissolving calcium carbonate is formed on the surfaces of the particles by the reaction of carbon dioxide with excess calcium ion present in the particles. This calcium carbonate slows the dissolution of the particles and the release of hemocyanin from the particles in vivo. An alternative method of forming calcium carbonate on the particles would be to express them to the vapors of a volatile carbonate such as ammonium carbonate during spray drying or in a vacuum chamber. This would have the advantage of not greatly shifting the pH of the particles as the ammonium carbonate would react with calcium chloride to make calcium carbonate and volatile ammonium chloride.

EXAMPLE 16

Slow Dissolving Fatty Acid Salt Particles

The excess calcium chloride formula of Example 8 can be further modified by the addition of sodium stearate to the phospholipid, by substituting 10% of the weight of phospholipid with an equal weight of sodium stearate before dispersing and homogenization. Upon spray drying, some of the excess calcium ion will form water insoluble calcium stearate within the particle which will slow its dissolution and release the active agent contained within the particle. Other fatty acids or fatty acid salts that form water insoluble calcium salts are also contemplated.

EXAMPLE 17

Avoiding Precipitation and Competing Ion Effects

It is contemplated that acceptable particles can be formed from the formula of Example 9, sample 6 if the calcium chloride content of the particles in moles is raised to more than the total number of moles of phospholipid plus twice the number of moles of albuterol sulfate and a modified spray drier atomizer nozzle is employed to mix the calcium ion containing solution B with a premixed preparation comprised of the combined mixtures of solutions A and C (phospholipid, albuterol sulfate containing solutions) immediately before atomization in the spray drier. The stable particles thus formed contain an excess of calcium ion to overcome the competing effects of the sulfate ion and thus still form the metal ion-lipid complexes described above. Mixing the sulfate containing solution with the calcium ion containing solution immediately before spray drying, this avoids the negative effects of calcium sulfate precipitation on the atomization process and thus the particle size distribution.

EXAMPLE 18

Treatment of Diabetes with Insulin Containing Metal Ion-Lipid Microparticle

Example 18 shows how the present invention can be used to treat Type I or Type II diabetes in human or animal subjects.

In this Example, treatment of patients suffering from Type I or Type II diabetes is demonstrated using the insulin containing microparticle of Example 12. After formation, the insulin containing microparticle composition of Example 12 is introduced into a holding chamber of a DPI, pMDI, nebulizer, insufflator or liquid dose inhaler and is aerosolized by any conventional means. The insulin containing microparticle is then introduced into the lungs of a subject by the patient inhaling on the mouthpiece of the DPI or pMDI by taking long, deep breaths to draw the aerosolized dispersion into the lungs.

This method of introducing aerosolized insulin containing microparticles into the lungs of a patient to treat diabetes has many advantages over subcutaneous injections of insulin such as ease of use, rapid insulin absorption and rapid glucose response. The efficiency of systematic insulin delivery by this method is thought to be in the range of about 40%-60%. Individual dosages of insulin, per inhalation, depend on the weight ratio of insulin in the particular microparticle, but is generally within the range of 0.25 mg to 5 mg per inhalation. Generally, the total dosage of insulin desired during a single respiratory administration will be in the range from about 0.5 mg to about 20 mg of insulin.

Dosages of insulin, which are always expressed in USP units, must be based on the results of blood and urine glucose determinations and must be carefully individualized to attain optimum therapeutic effect. General guidelines on the dosage of insulin containing microparticles of the present invention administered intrapulmonary for treatment of juvenile diabetes in pediatric patients per single respiratory administration is approximately 1-1.5:1 by weight of insulin administered by the metal ion lipid particle of the present invention to the weight of insulin introduced by subcutaneous injections. For adult patients, the ratio is approximately 2:1.

EXAMPLE 19

Administration of Human Growth Hormone

Example 19 shows how the present invention can be used to administer human growth hormone in human and animal subjects.

In this Example, administration of sermorelin acetate (which is the acetate salt of an amidated synthetic 29 amino acid peptide, GRF 1-29-NH$_2$) is demonstrated for treatment of idiopathic growth hormone deficiency in children with growth failure. A metal ion-lipid microparticle is formed according to the teachings of Example 12 (without the step of acidifying with HCl) by substituting sermorelin acetate for insulin. The sermorelin acetate containing microparticle composition is then introduced into a holding chamber of a DPI, pMDI, nebulizer, insufflator or liquid dose inhaler and is aerosolized by any conventional means. The sermorelin acetate containing microparticle is then introduced into the lungs of a subject by the patient inhaling on the mouthpiece of the DPI or pMDI by taking long, deep breaths to draw the aerosolized dispersion into the lungs.

Dosages of sermorelin acetate containing microparticle is generally in the range of 0.02-0.04 mg/kg of body weight once a day before bedtime. Treatment should be discontinued when the epiphyses are fused. Height should be monitored monthly and care should be taken to ensure that the child grows at a rate consistent with the child's age. Patients who fail to respond should be evaluated to determine cause of unresponsiveness.

EXAMPLE 20

Administration of Tobramycin

Example 20 shows how the metal ion-lipid based microparticles of the present invention can be used for the administration of various antibiotics.

When a patient on mechanical ventilation has developed a nosocomial pneumonia and high pulmonary concentrations of antibiotics without systemic levels are desired, pulmonary delivery of antibiotics through a DPI, pMDI, insufflator, liquid dose inhaler or nebulizer may be desirable. Pulmonary delivery of antibiotics could also be useful when usage of broad spectrum antibiotics present toxicity problems. Antibiotics such as aminoglycosides (e.g., tobramycin), ansamycins (e.g., rifamycin), penicillins, chloramphenicol group antibiotics, peptides (e.g., vancomycin), linosamides (e.g., lyncomycin), macrolides (e.g., erythromycin) and tetracyclines (e.g., tetracycline) may be combined with the metal ion-lipid microparticle of the present invention for pulmonary administration. It is believed that formulations can be made that permit or disallow systemic absorption, depending on the clinical need.

In this Example, administration of tobramycin is demonstrated for the treatment of bacterial pneumonia. A metal ion-lipid microparticle is formed according to the teachings of Example 7, sample 5 where commercially available tobramycin free base is substituted for lactose. The resulting tobramycin metal ion-phospholipid complex is introduced into a holding chamber of a DPI, pMDI, nebulizer, insufflator or liquid dose inhaler and is aerosolized by any conventional means. The tobramycin metal ion phospholipid complex is then introduced into the lungs of a subject by the patient inhaling on the mouthpiece of the DPI or pMDI by taking long, deep breaths to draw the aerosolized dispersion into the lungs.

Depending on the stage and seriousness of pneumonia and assuming normal renal function, dosages in adults can range from 0.5-1 mg/kg of tobramycin per administration every eight hours not to exceed 2.5 mg/kg/day.

EXAMPLE 21

Administration of Ethambutol

Example 21 shows the metal ion-lipid based microparticles of the present invention used with ethambutol as a tuberculostatic agent.

In a patient with pulmonary tuberculosis, it may be desirable to introduce a tuberculostatic agent directly into the site of infection. Systemic administration of ethambutol can be detrimental resulting in depigmentation of the tapetum lucidum of the eye and clinical visual loss. The administration of the drug directly to the pulmonary focus of infection would be expected to reduce the amount of drug systemically administered. In this Example, administration of ethambutol is demonstrated for treatment of pulmonary tuberculosis. A metal ion-lipid microparticle is formed according to the teachings of Example 7, sample 5 where commercially available ethambutol hydrochloride is substituted for lactose. The resulting ethambutol metal ion-phospholipid complex is introduced into the holding chamber of a DPI, pMDI, nebulizer, insufflator or liquid dose inhaler and is aerosolized by any conventional means. The ethambutol metal ion-phospholipid complex is then introduced into the lungs of a subject by the patient inhaling on the mouthpiece of the DPI or pMDI by taking long, deep breaths to draw the aerosolized dispersion into the lungs.

Depending on the stage of tuberculosis, dosages for adults can range from 15 mg/kg per 24 hour period of ethambutol hydrochloride for patients who have not received previous antitubercular therapy and 25 mg/kg per 24 hour period of ethambutol hydrochloride for adult patients who have had previous tuberculosis therapy. Administration should only be once a day. Ethambutol hydrochloride should not be used in children under thirteen years of age.

EXAMPLE 22

Administration of Ibuprofen

This Example shows the metal ion-lipid based microparticles of the present invention used with ibuprofen.

Due to the rapid bioavailability of intrapulmonary delivered drugs, it may be desirable to deliver an analgesic directly into the lungs. It may also be desirable to deliver an analgesic directly into the lungs to avoid GI complications which sometimes occur due to oral delivery of analgesics. In this Example, ibuprofen, a nonsteroidal anti-inflammatory and analgesic agent, is combined with the microparticle of the present invention according to the teachings of Example 7, sample 5. In combining ibuprofen with the metal ion-lipid microparticle of the present invention, commercially available ibuprofen may be used. The resulting ibuprofen metal ion phospholipid complex is introduced into a holding chamber of the DPI, pMDI, liquid dose inhaler, nebulizer or insufflator and is aerosolized by any conventional means. The ibuprofen containing microparticle composition is then introduced into the lungs of a subject by the patient inhaling on the mouthpiece of the DPI or pMDI by taking long, deep breaths to draw the aerosolized dispersion into the lungs.

Adult dosages can range from 100-150 mg of ibuprofen per inhalation for an adult subject, not to exceed 400-600 mg in a single respiratory administration for inflammatory conditions such as rheumatoid and osteoarthritis. Total dosage should not exceed 3 g daily. Dosages for juvenile arthritis should not exceed 400 mg daily for children weighing less than 20 kg, 600 mg for children weighing less than 20-30 kg and 800 mg daily for children weighing 30-40 kg. For relief of mild to moderate pain, the usual adult dosage is about 200 mg every 4-6 hours and may be increased if pain persists. For antipyresis in children from 6 months to 12 years of age, dosage should not exceed 7.5 mg/kg.

Other analgesics such as acetaminophen and aspirin may also be combined with the metal ion-lipid microparticle of the present invention according to the teachings of Example 7 and Example 22.

We claim:

1. A microparticle for drug delivery wherein the microparticle comprises an active agent and an excipient, wherein the active agent comprises an antibiotic, wherein the excipient comprises a metal ion-lipid complex, wherein the metal ion is chosen from the group consisting of lanthanide metals, actinide metals, group IIa and IIIb metals, transition metals or mixtures thereof, wherein the lipid comprises a phospholipid, and wherein the complex results in a glass transition temperature increase of the microparticle.

2. The microparticle of claim 1 wherein the microparticle has a glass transition temperature of at least 20° C. above a storage temperature for the drug or active agent.

3. The microparticle of claim 1 wherein the phospholipid is chosen from the group consisting of DPPC, DSPC, DMPC, dioctylphosphatidycholine, soy phosphatidylcholine, egg phosphatidylcholine and partially hydrogenated phosphatides and polymerizable phospholipids.

4. The microparticle of claim 1 wherein the presence of the metal ion raises the glass transition temperature of the microparticle at least 2° C. above that of the same microparticle without the metal ion.

5. The microparticle of claim 4 wherein the metal ion is chosen from the group consisting of calcium, zinc, aluminum, iron and magnesium in the form of water soluble salts and mixtures thereof.

6. The microparticle of claim 1 wherein the lipid component is comprised of a mixture of at least two lipids.

7. The microparticle of claim 1 wherein the microparticle has a mean volume aerodynamic particle size of about 0.5 μm to 7 μm.

8. A composition comprising a plurality of microparticles of claim 7.

9. The microparticle composition of claim 8 wherein the microparticles are substantially non-hollow and non-porous.

10. The microparticle composition of claim 9 further comprising a powder modifying agent.

11. The microparticle composition of claim 10 wherein the powder modifying agent is a carbohydrate.

12. The microparticle composition of claim 11 wherein the carbohydrate is selected from the group consisting of lactose, sucrose, hydroxyl ethyl starch; hetastarch, trehalose, mannose and mannitol.

13. A stable microparticle composition for drug delivery wherein the microparticle is comprised of a metal ion-lipid complex formed by the following process: dispersing a phospholipid in water to create a first preparation; suspending a metal compound or salt in water to create a second preparation; adding an antibiotic; combining the first and second preparations; and spray drying the combined preparations to create a stable metal ion-lipid microparticle composition.

14. The microparticle composition of claim 13 wherein the phospholipid is selected from the group consisting of soy phosphatidylcholine, egg phosphatidylcholine, DPPC, DSPC, DMPC, dioctylphosphatidylcholine, and partially and fully hydrogenated phosphatides.

15. The microparticle composition of claim 13 wherein the metal ion is added in the form of calcium salt.

16. The microparticle composition of claim 13 wherein the combined preparation is spray dried with an inlet temperature within the range of 40-100° C. and an outlet temperature within the range of 30-85° C.

17. The microparticle composition of claim 13 wherein the antibiotic is added to one of the preparations selected from the group consisting of the first preparation, the second preparation and the combination of the first and second preparation.

18. The microparticle composition of claim 13 wherein the drug or active agent is added to the formed metal ion-lipid complex.

19. The microparticle composition of claim 13 wherein the antibiotic comprises tobramycin.

20. The microparticle of claim 1 wherein the active agent comprises a plurality of active agents.

21. The microparticle of claim 1 wherein the excipient comprises a plurality of excipients.

22. The microparticle of claim 1 wherein the complex results in a glass transition temperature increase sufficient to stabilitize against water sorption.

23. The microparticle of claim 1 wherein the antibiotic comprises tobramycin.

\* \* \* \* \*